(12) United States Patent
Johnson

(10) Patent No.: US 7,435,431 B2
(45) Date of Patent: Oct. 14, 2008

(54) METHOD FOR CONTROLLING BODY WEIGHT IN ESTROGEN-INSUFFICIENT WOMEN

(75) Inventor: Catherine D. Johnson, Dublin, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/643,320

(22) Filed: Dec. 21, 2006

(65) Prior Publication Data
US 2007/0098821 A1 May 3, 2007

Related U.S. Application Data

(63) Continuation-in-part of application No. 11/188,464, filed on Jul. 25, 2005.

(60) Provisional application No. 60/591,656, filed on Jul. 28, 2004.

(51) Int. Cl.
*A61K 36/736* (2006.01)
(52) U.S. Cl. .................................. 424/735; 514/23
(58) Field of Classification Search ................... None
See application file for complete search history.

(56) References Cited

U.S. PATENT DOCUMENTS

| | | | |
|---|---|---|---|
| 5,612,074 A | 3/1997 | Leach | |
| 5,830,887 A | 11/1998 | Kelly | |
| 5,900,255 A | 5/1999 | Ohta et al. | |
| 6,340,703 B1 | 1/2002 | Kelly | |
| 6,355,250 B1 | 3/2002 | Patel et al. | |
| 6,375,994 B1 | 4/2002 | Paul et al. | |
| 6,391,309 B1 | 5/2002 | Empie et al. | |
| 6,436,446 B1 | 8/2002 | Forusz et al. | |
| 6,551,630 B2 | 4/2003 | Patel et al. | |
| 6,638,540 B2 | 10/2003 | Muhlbauer | |
| 2004/0137112 A1 | 7/2004 | Katz et al. | |
| 2005/0079232 A1 | 4/2005 | Offord-Cavin et al. | |
| 2007/0010480 A1* | 1/2007 | Rusing et al. | ........ 514/54 |

FOREIGN PATENT DOCUMENTS

| | | |
|---|---|---|
| JP | 1120275 | 5/1989 |
| WO | WO 99/07239 | 2/1999 |
| WO | WO 00/10402 | 3/2000 |
| WO | WO 02/052954 A3 | 7/2002 |
| WO | WO 03/053167 A1 | 7/2003 |
| WO | WO 2004/105516 | * 12/2004 |

OTHER PUBLICATIONS

"Prune" website (http://web.archive.org/web/20030104152828/http://www.whfoods.com/genpage.php?tname=foodspice&dbid=103—web archived version from Jan. 2004).*
http://www.whfoods.com/genpage.php?pfriendly=1&tname=nutrientprofile&dbid=116—accessed Jan. 17, 2008.*

U.S. Appl. No. 11/188,464, filed Jul. 25, 2005, Catherine D. Johnson.
Flaxseed Supplementation Positively Influences Bone Metabolism in Postmenopausal Women, Bahran J. Arjmandi, et al, vol. 1, No. 2 JANA 27, Fall 1998.
Soy Protein and Isoflavones: Their effects on blood lipids and bone density in postmenopausal women, Susan M Potter, et al, Am J Clin Nutr, 1998; 68(suppl): 1375S-9S.
Soybean Isoflavones Dose-Dependently Reduce Bone Turnover but Do Not Reverse Established Osteopenia in Adult Overiectomized Rats, Picherit, et al, J. Nutr. 131: 723-728, 2001.
Role of Soy Protein with Normal or Reduced Isoflavone Content in Reversing Bone Loss Induced by Ovarian Hormone Deficiency in Rats, Arjmandi, et al, Am. J Clin. Nutr. 1998;68 (suppl): 1358S-63S.
Prunes Test Highest in Important Health-Sustaining Compounds, Plum Good News, vol. XI, The California Prune Board.
Dried Plums Create the Perfectly Balanced Energy Bar: Perfect Nutrition . . . Perfect Taste and Texture, California Prune Board Food Technology, Technical Bulletin, May, 1999.
Various Selected Vegetables, Fruits, Mushrooms and Red Wine Residue Inhibit Bone Resorption in Rats, Roman C. Muhlbauer, et al, J. Nutr. 133: 3592-3597, 2003.
True Calcium Absorption in the Intestine is Enhanced by Fructooligosaccharide Feeding in Rats, Tomio Morohashi et al, J. Nutr. 128: 1815-1818, 1998.
Effect of Acetate and Propionate on Calcium Absorption from the Rectum and Distal Colon of Humans, Trinidad P Trinidad, et al, Am. J. Clin Nutr 1996;63:574-8.
Nondigestible oligosaccharides do not interfere with calcium and nonheme-iron absorption in young, healthy men, Ellen GHM van den Heuvel, et al, Am J Clin Nutr 1998;67:445-51.
Prune: Its Efficacy in Prevention of Ovarian Hormone Deficiency-Induced Bone Loss, B.H. Arjmandi, et al, (SU334 Abstract), S515, 1999.
Prune Dose-Dependently Reverses Bone Loss in Ovarian Hormone Deficient Rats, F. Deyhim, et al, (SA344 Abstract) S394, 1999.
Dietary Fructooligosaccharides Improve Soy-Osteopenia Prevention in the Ovariectomized Rat, J. Mathey et al, (SU358 Abstract).
Effects of Soy, Fructooligosaccharide, and their Combination on Reversal of Bone Loss in Ovariectomized Osteopenic Rats, L.J. Hammond, et al, (SU364 Abstract).
Flaxseed Improves Lipid Profile without Altering Biomarkers of Bone Metabolism in Postmenopausal Women, Edralin A. Lucas, et al, J Clin Endocrinol Metab 87: 1527-1532, 2002.
Exposure to purified lignan from flaxseed (Linum usitatissimum) alters bone development in female rats, Wendy E. Ward, et al, British Journal of Nutrition (2001), 86, 499-505.

(Continued)

*Primary Examiner*—Susan C Hoffman
(74) *Attorney, Agent, or Firm*—William J. Winter; Sandra E. Weida

(57) ABSTRACT

Disclosed are methods of controlling body weight in estrogen-insufficient women by administering compositions comprising (A) those dried fruit solids that inherently comprise flavonoids, hydroxycinnamic acids, and a fiber component of which at least about 20% by weight is soluble fiber, and (B) a soluble, indigestible oligosaccharide in addition to any soluble fiber inherently in the dried fruit solids. The dried fruit solids may also be characterized as those selected from dried plum, dried grape, dried date, or dried fig. Administration of dried fruit solids (e.g., dried plum solids) in combination with soluble indigestible oligosaccharides (e.g., fructooligosaccharides) are surprisingly effective in controlling body weight gain in estrogen-insufficient women.

14 Claims, No Drawings

OTHER PUBLICATIONS

Early exposure to flaxseed or its purified lignan affects the femur properties of female but not male rats, W. E. Ward, et al, Abstract 163.6 from Nutrients and Bone Mineral Metabolism A224.

A Combination of Dietary Fructooligosaccharides and Isoflavone Conjugates Increases Femoral Bone Mineral Density and Equol Production in Ovariectomized Mice, Atsutane Ohta, et al, J. Nutr. 132: 2048-2054, 2002.

Dried Plums Improve Indices of Bone Formation in Postmenopausal Women, Bahram H. Arjmandi, et al, J or Women's Health & Gender—Based Medicine, vol. 11, No. 1, 2002.

Chemical Composition and Potential Health Effects of Prunes: A Functional Food? Stacewicz-Sapuntzakis M, Crit. Rev Food Sci Nutr. May 2001; 41(4):251-86.

A Combination of Dietary Fructooligosaccharides and Isoflavone Conjugates Increases Femoral Bone Mineral Density and Equol Production in Ovariectomized Mice, Ohta A, et al, J Nutr. Jul. 2002; 132(7):2048-54 (Abstract).

Differential Effects of Dietary Flaxseed Protein and Soy Protein on Plasma Triglyceride and Uric Acid Levels in Animal Models, Bhathena SJ, et al, J Nutr Biochem, 2002 Nov. 13(11):684-689. (Abstract).

Supplementation with Flaxseed Alters Estrogen Metabolism in Postmenopausal Women to a Greater Extent than Does Supplementation with an Equal Amount of Soy, Brooks JD, et al, Am J Clin Nutr. Feb. 2004; 79(2):318-25. (Abstract).

Combination of Soy and Sub-Optimal Dose of 17β-Estradiol May Reverse Bone Loss in a Rat Model of Postmenopausal Osteoporosis, L. Devareddy, et al, M372 Abstract, J Bone Miner Res, 18(2):S384 2003.

Dietary Fructooligosaccharides Modify Intestinal Bioavailability of a Single Dose of Genistein and Daidzein and Affect Their Urinary Excretion and Kinetics in Blood Rats, Mariko Uehara, et al, J. Nutr. 131: 787-795, 2001.

Bioavailability, Disposition, and Dose-Response Effects of Soy Isoflavones When Consumed by Healthy Women at Physiologically Typical Dietary Intakes, Kenneth D.R. Setchell, et al, J. 133: 1027-1035, 2003.

Evaluation of the Effect of Soybean Milk and Soybean Milk Peptide on Bone Metabolism in the Rat Model with Ovariectomized Osteoporosis, Naomi Omi, et al, J. Nutr. Sci. Vitaminol, 40, 201-211, 1994.

Isoflavone-rich soy protein isolate attenuates bone loss in the lumbar spine of perimenopausal women, D Lee Alekel, et al, Am J. Clin Nutr. 2000;72:844-52.

Whole Flaxseed Consumption Lowers Serum LDL-Cholesterol and Lipoprotein(a) Concentrations in Postmenopausal Women, Bahram H. Arjmandi, et al, Nutrition Research, vol. 18, No. 7 pp. 1203-1214, 1998.

Effects of Fructooligosaccharides on Bone and Mineral Absorption in the Rat Model with Ovariectomized Osteoporosis, Azusa Taguchi, et al, Nov. 1, 1994.

Dietary Soybean Protein Prevents Bone Loss in an Ovariectomized Rat Model of Osteoporosis, Bahram H. Arjmandi, et al, J. Nutr. 126: 161-167, 1996.

Oligofructose Stimulates Calcium Absorption in Adolescents, Ellen GHM van den Heuvel, et al, Am. J. Clin. Nutr., 1999; 69-544-8.

Fructooligosaccharide Consumption Enhances Femoral Bone Volume and Mineral Concentrations in Rats, Sawa Takahara, et al, J. Nutr. 130: 1792-1795, 2000.

A Randomized Study on the Effects of Estrogen/Gestagen or High Dose Oral Calcium on Trabecular Bone Remodeling in Postmenopausal Osteoporosis, T. Steiniche, et al, Bone, 10, 313-320 (1989).

Raloxifene Inhibits Bone Turnover and Prevents Further Cancellous Bone Loss in Adult Ovariectomized Rats with Established Osteopenia, Glenda L. Evans, et al, Endocrinology, vol. 137, No. 10, 4139-4144, 1996.

[P-44] Abstract #97.061, Soy Phytoestrogens and Bone, Pansini F, et al, NAMS, 1997.

Carbohydrate Composition of Selected Plum/Prune Preparations, Cheryl L. Dikeman et al, Journal of Agricultural and Food Chemistry, 2004, 52, 853-859, XP009056020.

Raisin Dietary Fiber Composition and In Vitro Bile Acid Binding, Mary E. Camire et al, Journal of Agricultural and Food Chemistry, 2003, 51, 834-837. XP009056021.

Dietary Fibre Content of Dates From 13 Varieties of Date Palm Phoenix Dactylifera L., Walid Al-Shahib, et al, International Journal of Food Science and Technology, 2002, 37, 719-721. XP009056028.

Dried Plum Improves Micro-Structural Properties of Trabecular Bone Following Ovarian Hormone Deficiency, Farzad Deyhim et al, Experimental Biology 2003: Abstracts. XP009056028.

Dried Figs Contain More Dietary Fiber Than Most Fruits, Cereals . . . Figs Rank First in 8 Nutrient Categories, Dean D. Duxbury, Food Processing, May 1988, 60-61. XP009056032.

California Dried Plums: Pastes, Purees, Butters, available http://www.californiadriedplums.org/Foodservice/Products/ProductDetail/?contentId=366 (downloaded Nov. 14, 2007).

* cited by examiner

METHOD FOR CONTROLLING BODY WEIGHT IN ESTROGEN-INSUFFICIENT WOMEN

CROSS-REFERENCE TO RELATED APPLICATION

This application is a continuation in part of U.S. patent application Ser. No. 11/188,464, filed Jul. 25, 2005, which makes reference to and claims the benefit of U.S. Provisional Patent Application 60/591,656, filed Jul. 28, 2004.

FIELD OF THE INVENTION

The present invention relates to nutritional compositions comprising a soluble, indigestible oligosaccharide in combination with certain dried fruit solids. The compositions are useful in treating or preventing osteoporosis, including the reversal of osteopenia and the prevention of bone loss, and for controlling body weight in estrogen-insufficient women.

BACKGROUND OF THE INVENTION

Millions of people are afflicted with osteoporosis, a condition or disease characterized by low or reduced bone mineral density, which often results in painful and sometimes life-threatening bone fractures.

Osteoporosis can be classified as either primary or secondary. Primary osteoporosis is associated with menopause (natural, premature, or surgical), aging, or both. Secondary osteoporosis is associated with medical conditions such as Paget's, chronic renal disease, amenorrhea from eating disorders, transplantation, hyperthyroidism, parathyroidism, and others. Secondary osteoporosis can also be associated with the use of certain medications, such as various cancer chemotherapies, gonadotropin releasing hormone agonists, medroxy progesterine acetate for birth control, corticosteroids, anticonvulsants, and others.

There are many different methods of treating or preventing osteoporosis that are known or otherwise described in the literature, including estrogen therapy in postmenopausal women, the administration of calcitonin, parathyroid hormone, bisphosphonates, or other similar medications or therapies in appropriate individuals. The use of many of these medications, however, is often associated with its own inherent risk and side effect profile, most notable of which is perhaps the use of estrogen in postmenopausal women and the recently documented concerns associated with such use.

Other methods of treating or preventing osteoporosis include a variety of dietary management methods directed to the use of different nutrients or other natural materials. Most notable among these dietary methods is the use of calcium and vitamin D to correct or prevent their respective insufficiencies in individuals at risk of developing osteoporosis. Current recommendations are that all adults receive at least 1200 mg/day of calcium and from 400-800 IU/day of vitamin D.

Other dietary methods for treating or preventing osteoporosis include the use of a variety of different nutrients or other natural materials, including those described in: U.S. Pat. No. 6,638,540 (use of plant extracts from onions, parsley, cabbage, arrugula or roquette); U.S. Pat. No. 6,391,309 (use of plant phytochemicals such as isoflavones, lignans, saponins, sapogenins, catechins and phenolic acids, preferred sources of which include soy, wheat, psyllium, rice, oats, red clover, kudzu, alfalfa, flax, and cocoa); U.S. Pat. No. 6,340,703 (use of soy isoflavone formononetin); U.S. Pat. No. 5,830,887 (use of natural phyto-estrogens including genistein, diadzein, formononetin and biochanin A, which may be obtained from soy); U.S. Pat. No. 6,436,446 B1 (use of calcium, an organic acid, and isoflavone and inulin or an oligosaccharide to reduce the risk of bone density loss; soy is disclosed as a possible source of the isoflavones; ogliosaccharides include FOS and gluco-oligosaccharides); and WO 02/074308 (use of soy or other isoflavones such as diadzein, glycitein and genistein in combination with polyunsaturated acids to prevent osteoporosis)

Still other dietary methods for treating or preventing osteoporosis are described in U.S. Pat. No. 5,612,074 discloses a nutrient fortified food bar with dietary fiber, non-animal protein, simple carbohydrates, complex carbohydrates, sugars, antioxidants and lecithin that provides polyunsaturated linoleic acid, superunsaturated alpha-linolenic acid, amino acids, magnesium, chloropolyll and pyridoxine and includes sodium and potassium, but has no cholesterol, artificial flavorings or colors and has a minimum amount of saturated fat. Various sources are disclosed for the dietary fiber including oatmeal, cornmeal, wheat germ, barley, rye, psyllium husk, apple pectin, spelt flour, kamut flour, and dried unsulphured date, fig, papaya, raisin, apricot, pineapple, banana, mulberry, cherry, prune, sultana, and pineapple. Non-animal protein sources include soy, wheat germ, gelatin, yeast, almond, hulled sesame seed, sunflower seed, flaxseed, oatmeal and whey.

WO 01/97633 discloses food products with vitamins, minerals, soy protein, soluble fiber and calcium. The products comprise at least one particulate ingredient, a nutrient powder and a binder. The particulate ingredient cad-provide macronutrients such as soy proteins, fiber, calcium, lipids and other protein sources. Suitable particulate ingredients can be sourced from grain flakes, soy flour, soy protein, soy protein isolate, peanut flour, oat bran, guar gum, psyllium, fructooligosaccharides (such as inulin) and/or insoluble fiber such as from bran or carboxymethylcellulose. The particulate ingredient can include nuts or nut pieces, or dried fruit pieces. Examples of suitable dried fruits include raisins, prunes, cherries, apples, pineapple, watermelon, cantaloupe, figs, bananas, dates, currants, apricots, dried cranberries and mixtures thereof.

Still other methods of treating or preventing osteoporosis have been directed to the dietary use of fructooligosaccharides (FOS), an example of which is described in U.S. Pat. No. 5,900,255, which discloses a material for the prevention and treatment of osteoporosis that contains minerals and digestible oligosaccharides such as FOS.

Other dietary methods include the use of plums or prunes to affect bone mineral density. For example, according to one study, ovariectomized rats were immediately fed different levels (5% and 25%) of dried plum for 45 days. The bone mineral density (BMD) of the 4th lumbar in rats eating a high dose of dried plum was similar the BMD of the sham operated group (Arjmandi et al., "Prune: Its Efficacy in Prevention of Ovarian Hormone Deficiency-Induced Bone Loss," J.B.M.R 1999; 14: S515). Dried plum at 5, 15, or 25% of diet was also able to reverse existing bone loss in a dose dependent manner in another study of ovarian hormone deficient rats. This study also showed that the strength of the bones was greater in the rats fed any concentration of dried plums compared to the control groups (Deyhim, F., et al., "Prune Dose-Dependently Reverses Bone Loss in Ovarian Deficient Rats," J. Bone & Mineral Research 1999; 14: S394). Muhlbauer et al., study the effect of various foods, including prunes, on male rats and found that feeding rats dry fennel, celeriac, oranges, prunes, French beans and mushrooms as well as the freeze-dried residue from red wine inhibited bone resorption. (Muhlbauer, Roman C., et al., "Various Selected Vegetables, Fruits, Mushrooms and Red Wine Residue Inhibit Bone Resorption in Rats," J. Nutr. 2003; 133: 3592-3597.)

In another study, 100 grams of dried plums were fed to postmenopausal women for 3 months (Arjmandi, B. M., et al., "Dried Plums Improve Indices of Bone Formation in Postmenopausal Women," J. Women's Health & Gender Based Medicine 2002; 11: 61-68). Serum levels of insulin-like growth factor and bone specific alkaline phosphatase were significantly increased. Although these markers are associated with greater rates of bone formation, the biomarkers of bone resorption were not affected. The results of this study suggest that dried plums may exert positive effects on bone in postmenopausal women but probably not by decreasing the rate of bone remodeling which is accelerated in postmenopausal women.

Although dried plums are known to be effective in improving certain indices of bone formation, many people dislike dried plums or are otherwise unwilling to take enough of them each day to affect bone formation, i.e., 100 gms or about 10 dried plums daily. For these people, it would be desirable to formulate the dried plums into a product form such as a beverage or a snack or meal bar. However, because such large quantities of dried plums are needed, formulating a convenient product form such as a beverage or meal bar with enough dried plum solids to affect bone formation has been problematic.

It has now been found that the combination of dried fruit solids as defined herein and a soluble indigestible oligosaccharide are surprisingly more effective in treating or preventing osteoporosis than either component when used alone. In particular, it has been found that the combination of fructooligosaccharides and dried plums is many times more effective in changing bone mineral density in estrogen-deficient, ovariectomized, osteopenia-induced, female rats than either ingredient when used alone.

It has also been found that these combinations of dried fruit solids and soluble indigestible oligosaccharides are surprisingly effective in controlling body weight in estrogen-insufficient animal models. It is well known that estrogen insufficiency associated with menopause, surgical ovariectomy, ovarian disorders and certain drug treatments often results in or contributes to weight gain as well as osteoporosis. It is also well known that weight reduction by traditional caloric restriction techniques in postmenopausal women is often slower because of lower basal metabolic rates, as well as a compromised hormonal status. Both menopause and weight reduction are associated with bone loss.

SUMMARY OF THE INVENTION

The present invention includes those embodiments directed to nutritional compositions and methods of using the compositions for treating or preventing osteoporosis, controlling body in estrogen-insufficient women, or both. The nutritional compositions comprise (A) dried fruit solids that inherently comprise flavanoids, hydroxycinnamic acids, and a fiber component of which about 20% by weight is soluble fiber, and (B) a soluble, indigestible oligosaccharide in addition to the dried fruit fiber. These dried fruit solids can also be characterized as those selected from dried plums, dried grape, dried fig, dried date, or combinations thereof.

It has been found that the combination of dried fruit solids and soluble indigestible oligosaccharides, as defined herein, are surprisingly more effective in increasing bone mineral density than either component when used alone, and that the combination is also effective in controlling body in estrogen-insufficient animal models. The nutritional compositions of the present invention may, therefore, now be formulated with reduced concentrations of dried fruit solids, while still maintaining an ability to affect bone mineral density, and control body gain, provided that the dried fruit solids are used in combination with the soluble indigestible oligosaccharide component described herein.

The present invention is based upon animal studies in which combinations of a soluble, indigestible oligosaccharide (e.g., fructooligosaccharides) and dried fruit solids (e.g., dried plum solids) resulted in a significant improvement in bone mineral density in the animal models studied, as well as reductions in body weight gain in an estrogen-deficient animal model.

DETAILED DESCRIPTION

The nutritional compositions of the present invention, as well as the corresponding methods of using those compositions, include as essential elements or limitations, a soluble indigestible oligosaccharide and dried fruit solids as defined herein. These and other essential or optional elements or limitations of the compositions and methods of the present invention are described in detail hereinafter.

The term "estrogen-insufficient individual" as used herein means women who experience lower than normal or otherwise reduced estrogen levels, including complete estrogen deficiencies. This may include women who suffer from estrogen insufficiency caused by ovarian disorders, menopause, surgical ovariectomy, or by administration of drugs.

The term "osteoporosis" as used herein, unless otherwise specified, refers to any decrease or reduction in bone mineral density in an individual, and includes both osteoporosis and osteopenia as defined by the World Health Organization (WHO). The WHO has defined acceptable bone mineral density as that which falls within one standard deviation of a normal value or corresponds to a T score greater than −1. The WHO has defined osteopenia by a bone mineral density within 1 to 2.5 standard deviations of normal or that which corresponds to a T score of from −1 to −2.5. The WHO has characterized osteoporosis as a more severe form of osteopenia, and has defined it by a bone mineral density of less than 2.5 standard deviations from normal or that which corresponds to a T score of less than −2.5.

The terms "treatment" and "treatment and prevention" are used interchangeably herein and, unless otherwise specified, refer to methods directed to individuals afflicted by or otherwise at risk of developing osteoporosis, and means any method of affecting bone mineral density or structure in an individual, which includes increasing bone mineral density, slowing the rate or onset of bone mineral density reduction, maintaining current bone mineral density, or reversing some or all of bone mineral density reductions or insufficiencies in individuals otherwise afflicted with osteoporosis.

The term "lipid" as used herein, unless otherwise specified, means fats, oils, and combinations thereof.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

Any reference to singular characteristics or limitations of the present invention shall include the corresponding plural characteristic or limitation, and vice versa, unless otherwise specified or clearly implied to the contrary by the context in which the reference is made.

Any combination of method or process steps as used herein may be performed in any order, unless otherwise specified or clearly implied to the contrary by the context in which the referenced combination is made.

The compositions and methods of the present invention may be substantially free of any specific ingredient described herein, provided that the remaining composition comprises all of the essential limitations as defined herein. In this context, the term "substantially free" means that the compositions typically comprise less than about 2%, including less than about 0.5%, also including less than about 0.1%, and also including zero percent, by weight of the identified ingredient.

The compositions and methods of the present invention may comprise, consist of, or consist essentially of the essential elements and limitations of the invention described herein, as well as any additional or optional ingredients, components, or limitations described herein or otherwise useful in a nutritional or pharmaceutical application.

Product Form

The nutritional compositions for use herein may be formulated and administered in any known or otherwise suitable oral product form. Any solid, liquid, or powder form, including combinations or variations thereof, are suitable for use herein, provided that such forms allow for safe and effective oral delivery to the individual of the essential ingredients as also defined herein.

The nutritional compositions of the present invention include any product form comprising the essential ingredients described herein, and which is safe and effective for oral administration. The nutritional compositions may be formulated to include only the essential ingredients described herein, or may be modified with optional ingredients to form a number of different product forms. The nutritional compositions of the present invention are preferably formulated as dietary product forms, which are defined herein as those embodiments comprising the essential ingredients of the present invention in a product form that then contains fat, protein, and carbohydrate, and preferably also contains vitamins, minerals, or combinations thereof.

The nutritional compositions of the present invention may therefore include a variety of different product forms, including most any conventional or otherwise known food product form, some non-limiting examples of which include confectionary products, cereals, food condiments (e.g., spreads, powders, sauces, jams, jelly, coffee creamer or sweetener), pasta, baking or cooking materials (e.g., flour, fats or oils, butter or margarine, breading or baking mixes), salted or seasoned snacks (e.g., extruded, baked, fried), beverages (e.g., coffee, juice, carbonated beverage, non-carbonated beverage, tea, ice-cream based drinks), snack or meal replacement bars (e.g., Slimfast™ bars, Ensure™ bars, ZonePerfect bars™, Glucerna™ bars), smoothies, breakfast cereals, cheeses, gummie products, salted or unsalted crisp snacks (e.g., chips, crackers, pretzels), dips, baked goods (e.g., cookies, cakes, pies, pastries, bread, bagels, croutons, dressings, dry mixes (e.g., mixes for muffins, cookies, waffles, pancakes, beverages), frozen desserts (e.g., ice cream, popsicles, fudge bars, crushed ice, frozen yogurt), pasta, processed meats (e.g., corn dogs, hamburgers, hotdogs, sausage, pepperoni), pizza, pudding, flavored or unflavored gelatin, refrigerated dough (e.g., cookies, bread, brownies), milk or soy-based smoothies, yogurt or yogurt-based drinks, frozen yogurt, soy milk, soups, vegetable-based burgers, and popcorn-based snacks.

The nutritional compositions of the present invention may also be formulated in product forms such as capsules, tablets, pills, caplets, gels, liquids (e.g., suspensions, solutions, emulsions), powders or other particulates, and so forth. These product forms preferably contain only the essential ingredients as described herein, optionally in combination with other actives, processing aids or other dosage form excipients.

The nutritional compositions of the present invention, when formulated as a dietary product form, may potentially provide either a sole source or a supplemental source of nutrition to an individual. In this context, a sole source of nutrition is one that can be administered once or multiple times each day to potentially provide an individual with all or substantially all their fat, protein, carbohydrate, mineral, and vitamin needs per day or during the intended period of administration. A supplemental source of nutrition is defined herein as a dietary source that does not provide an individual with a potentially sole source of nutrition.

The nutritional compositions of the present invention are preferably formulated as milk-based liquids, soy-based liquids, low-pH liquids, reconstitutable powders, nutritional bites (e.g., plurality of smaller dietary product dosage forms in a single package), or nutritional bars (snack or meal replacement).

Soluble, Indigestible Oligosaccharide

The nutritional compositions of the present invention must comprise a soluble, indigestible oligosaccharide. Such materials are well known for use in a variety of nutritional products and product applications, all of which are also suitable for use in the compositions and methods of the present invention, provide that such materials are suitable for oral administration and are compatible with the other essential and selected ingredients in the composition.

The soluble, indigestible oligosaccharide component of the present invention is separate from any similar oligosaccharide component inherently part of the dried fruit component described hereinafter. It has been found that the synergistic results obtained from the combination of the selected dried fruit component and the soluble indigestible oligosaccharide component of the present invention results from the separate addition of each to the formulation. In other words, although the dried fruit may contain similar oligosaccharide materials, such materials must be provided in addition to and separate from the oligosaccharide component of the present invention.

The soluble, indigestible oligosaccharides for use in the compositions and methods of the present invention are generally categorized in the chemical and nutrition arts as soluble fiber. In this context, the term "soluble" refers to the oligosaccharide component and its capacity to be solubilized in a buffer solution at a defined pH in accordance with the American Association of Cereal Chemists (AACC) Method 32-07, which method is well known in the nutrition and chemical arts. For example, an oligosaccharide or fiber source containing an oligosaccharide is considered soluble if at least 60% of the total dietary fiber therein is soluble fiber as determined by AACC Method 32-07.

The soluble, indigestible oligosaccharide for use in the compositions and methods of the present invention must also be indigestible, which means that the oligosaccharide is resistant to endogenous digestion in the human upper digestive tract. Indigestible oligosaccharides are generally those having a degree of polymerization of from 2 to 20, preferably from 6 to 18, including from 8 to 14, or a molecular weight less than about 3,600, or both.

The nutritional compositions of the present invention preferably comprise a sufficient quantity of soluble, indigestible oligosaccharide to provide an individual with from about 1 g to about 50 g, preferably from about 3 g to about 30 g, including from about 5 g to about 20 g, and also including form about 8 g to about 15 g, per day of the soluble, indigestible oligosaccharide.

The soluble, indigestible oligosaccharide preferably represents from about 1% to about 50%, more typically from about 10% to about 40%, including from about 20% to about 30%, by weight of carbohydrates in the nutritional composition.

For solid embodiments of the nutritional compositions of the present invention, including solid nutritional bars, the solid embodiments preferably comprise soluble, indigestible oligosaccharide in quantities ranging from about 1% to about 50%, including from about 3% to about 30%, also including from about 5% to about 20%, and also including from 8% to about 15%, by weight of the solid nutritional composition.

For liquid embodiments of the nutritional compositions of the present invention, including liquids derived from reconstituted powders, the liquid embodiments preferably comprise soluble, indigestible oligosaccharide in quantities preferably ranging from about 1% to about 30%, more preferably from about 3% to about 25%, including from about 5% to about 20%, and also including from 7.5% to about 15%, by weight of the liquid nutritional composition.

Non-limiting examples of suitable indigestible oligosaccharides for use herein include fructooligosaccharides (FOS), fructosans, xylooligosaccharides (XOS), alpha galactooligosaccharides (GOS), trarsgalactosyl oligosaccharides (TOS), soybean oligosaccharides, lactosugar, hydrolyzed inulin, polydextrose, and combinations thereof. FOS is preferred for most applications. GOS is preferred, however, for most low pH formulations, e.g. pH less than about 6.2.

Suitable sources of soluble, indigestible oligosaccharides are well known in the nutrition arts and are available for use in the compositions and methods of the present invention. For example, FOS is available from Golden Technologies Company (Golden, Colo.) and XOS is available from Suntory Limited of Osaka, Japan. GOS is available from Solabia, Pantin Cedex, France. TOS is available from Yakult Honsha Co., Tokyo, Japan. Soybean oligosaccharide is available from Calpis Corporation distributed by Ajinomoto U.S.A. Inc., Teaneck, N.J. Hydrolyzed inulin is available from Rhone-Poulenc, Inc, Cranbury, N.J. while polydextrose is available from A. E. Staley in Decatur Ill.

Dried Fruit Solids

The nutritional compositions of the present invention must comprise dried fruit solids, wherein the dried fruity solids are preferably defined as those identified by and comprising flavonoids, hydroxycinnamic acids, and a fiber component of which at least 20% by weight is soluble fiber.

Dried fruit solids suitable for use in the compositions of the present invention are preferably defined as those identified by and comprising a combination of flavonoids (e.g., quercetin, rutin, daidzin, genistin, epicatechin, 7-methoxycoumarin) and hydroxycinnamic acids (e.g., p-coumaric acid, caffeic, ferulic, chlorogenic, neochlorogenic), wherein the dried fruit solids also have a soluble fiber content of at least about 20% A, preferably from about 30% to about 70%, including from about 30% to about 50%, by weight of the total dietary fiber in the dried fruit solids. The total dietary fiber content of the dried fruit solids is preferably at least about 4 g per 100 g of the dried fruit solids, more preferably from about 5 g to about 15 g, including from about 5 g to about 13 g, and also including from about 6 g to about 11 g, of total dietary fiber per 100 g of the dried fruit solids.

The term "dried fruit" as used herein, unless otherwise specified, refers to fruits that have been subjected to an active or passive drying process, including passive or active sun drying methods, to thus preferably allow for the evaporation of a majority of the water from the corresponding ripe, undried fruit. The term "dried fruit" as used herein, therefore, excludes any and all ripe fruits that have not yet been subjected to such drying processes, or fruit that has been strained or pressed rather than dried, unless of course the strained or pressed fruit is also subjected to an adequate drying process. Only dried fruit as defined herein are believed to provide the desired product performance when used in combination with the soluble, indigestible, oligosaccharide component described herein.

The term "dried fruit solids" as used herein, unless otherwise specified, refers to the dried fruit component of the present invention, less water, and is characterized in this way to identify the presence, and in some instances the quantity, of the dried fruit component for use in the various nutritional embodiments of the present invention. It is understood, however, that dried fruit solids are most always formulated into the nutritional compositions of the present invention along with at least some water inherent in or otherwise added to the dried fruit component of the composition. Dried plum solids, for example, for use herein might be in the form of a dried plum powder containing less than about 5% by weight of water or even a plum puree containing about 25% by weight of water.

The nutritional compositions of the present invention preferably comprise sufficient dried fruit solids to provide an individual with from about 1 g to about 100 g, preferably from about 20 g to about 80 g, including from about 25 g to about 70 g, and also including form about 30 g to about 50 g, per day of dried fruit solids, wherein the amount of dried fruit solids actually refers to the amount of dried fruit solids, less water, provided by the composition in a single or divided dose. The total daily dried fruit solids are preferably contained in two individual product forms, e.g., two meal or snack bars per day.

For solid embodiments of the nutritional compositions of the present invention, the solid embodiments preferably comprise dried fruit solids in quantities ranging from about 1% to about 90%, preferably from about 15% to about 60%, including from about 20% to about 40%, and also including from 25% to about 35%, by weight of the solid nutritional composition.

For liquid embodiments of the nutritional compositions of the present invention, including liquids derived from reconstituted powders, the liquid embodiments preferably comprise dried fruit solids in quantities ranging from about 1% to about 50%, preferably from about 3% to about 35%, including from about 5% to about 30%, and also including from 7.5% to about 25%, by weight of the liquid nutritional composition.

Preferred dried fruit solids for use in the nutritional compositions of the present invention include dried plums, dried dates, dried grapes, dried figs, and combinations thereof.

Particularly preferred are figs belonging to *Picus carcica*, Wazeri, Sultani, or Kudata varieties; grapes belonging to *Vitus vinifera*, Thompson variety; plums belonging to *Prunus domestica*, d'Agen, California, or French varieties; or dates belonging to *Phoenix dactylifera*, Medjool, Deglet Noor, or Arecaceae varieties. Dried plums are most preferred.

The dried fruit solids suitable for use in the compositions of the present invention may also be defined, in the alternative, as those dried fruit solids derived from, or otherwise in the form of, whole dried fruit having with a total phenolic content of at least 5 mg, preferably at least about 9 mg, more preferably from about 10 mg to about 30 mg, including from about 11 mg to about 25 mg, as determined by mg of gallic acid equivalents per gram of whole dried fruit. In this context, whole dried fruit refers to those dried fruit solids in consumable product forms such as prunes (11-13 mg), raisins (9-12 mg), figs (9-10 mg), dates (5-6 mg), and so forth. Using this alternative definition of dried fruit solids, such solids may be formulated into the composition, even when used in powder or other highly processed raw material form, provided that the whole dried fruit from which the raw material was derived has the requisite total phenolic content as described herein.

The dried fruit solids for use in the compositions of the present invention preferably and most typically undergo a Maillard Browning Reaction during the drying process, and so the dried fruit solids preferably contain one or more compounds generated during such reactions, such compounds including 5-hydroxymethylfurfural (IF); 2-furoylmethyl-alanine; 2-furoylmethyl-arginine; 2-furoylmethyl-proline; 2-furoylmethyl-gamma-aminobutyric acid; benzaldehyde; ethyl cinnamate; 2-furancarboxaldehyde; furosine; and protocatechuic acid. The dried fruit solids suitable for use in the compositions and methods of the present invention preferably contain at least 1, more preferably from 2-5, including from 3-4, of these specific Maillard Browning Reaction compounds. It is believed that dried fruit solids that have undergone this type of reaction during the drying process are even more effective in providing the performance benefits described herein with respect to enhancing bone health.

Dried plum solids are preferred for use in the compositions and methods of the present invention. Non limiting examples of dried plum solids or sources thereof include prunes (dried plums), dried plum powder, prune/plum juice (including dried plum/prune juice and dried plum/prune juice) plum or prune paste, dried plum paste, whole dried plum solids, dried plum bits, dried plum butter, fresh plum puree, dried plum puree, prune extract, prune/plum juice concentrate, and combinations thereof.

Commercial sources of dried plum solids or sources of such solids are readily available and well known to one practicing in the nutrition and formulation arts. For example, dried plum, dried plum/prune juice, dried plum/prune concentrate (Plum Juicy™ 300), fresh plum concentrate (Plum Juicy™ 600), whole dried plum solids, dried plum puree, Plum Juicy™/USDA dried plum puree (Plum Juicy™ 100), low moisture dried plum puree (Plum Juicy™ 400), dried plum butter (Plum Juicy™ 700), fresh plum puree, diced dried plum puree and dried plum bits are available California Dried Plum Board (previously known as the California Prune Board), Pleasanton, Calif. Various forms and sources of dried plum solids are also available from Sunsweet Growers, Inc., Pleasanton, Calif.

Other suitable sources of dried fruit solids, including those derived from grapes, figs, or dates, are likewise well known in the nutrition arts, and thus available for use in the compositions and methods of the present invention.

The combination of dried fruit solids and soluble, indigestible oligosaccharide preferably represents at least about 20% by weight of the carbohydrate in the nutritional composition, more preferably at least about 30%, including from about 30% to 100%, and also including from about 50% to about 95%, and also including from about 60% to about 80%, by weight of the carbohydrates in the composition. The weight ratio of the dried fruit solids to the soluble, indigestible oligosaccharide in the composition may range from about 15:1 to about 1:15, including from about 8:1 to about 1:8, also including from about 5:1 to about 1:5, also including from about 3:1 to about 1:3, and also including from about 2:1 to about 1:2.

The dried fruit solids for use herein typically comprise mostly carbohydrates with only minor amounts, if any, of protein and fat.

Macronutrients

The nutritional compositions of the present invention may further comprise one or more optional macronutrients in addition to the essential ingredients described herein. The optional macronutrients include proteins, lipids, carbohydrates, and combinations thereof. The nutritional compositions are preferably formulated as dietary products containing all three macronutrients.

Macronutrients suitable for use herein include any protein, lipid, or carbohydrate or source thereof that is known for or otherwise suitable for use in an oral nutritional composition, provided that the optional macronutrient is safe and effective for oral administration and is otherwise compatible with the essential and other selected ingredients in the composition.

The concentration or amount of optional lipid, carbohydrate, and protein, in the nutritional compositions can vary considerably depending upon the particular product form (e.g., bars or other solid dosage forms, milk or soy based liquids or other beverages, reconstitutable powders) and the various other formulations and targeted dietary needs. These optional macronutrients are most typically formulated within any of the embodied ranges described in the following table.

| | Macronutrients* | | | | | |
|---|---|---|---|---|---|---|
| | Percentage of total calories | | | Wt/wt percent of Nutritional Composition | | |
| Nutrients** | A | B | C | A | B | C |
| Carbohydrate | 0-100 | 10-70 | 40-50 | 0-98 | 1-50 | 10-30 |
| Lipid | 0-100 | 20-65 | 35-55 | 0-98 | 1-30 | 3-15 |
| Protein | 0-100 | 5-40 | 15-25 | 0-98 | 1-20 | 2-10 |

*Each numerical value is preceded by the term "about"
**Ranges do not include dried fruit solids and soluble indigestible oligosaccharide A) Carbohydrate Optional carbohydrates suitable for use in the nutritional compositions may be simple, complex, or variations or combinations thereof, all of which are optionally in addition to the dried fruit solids and the soluble indigestible oligosaccharide as described herein. Non-limiting examples of suitable carbohydrates include hydrolyzed or modified starch or cornstarch, maltodextrin, glucose polymers, sucrose, corn syrup, corn syrup solids, rice-derived carbohydrate, glucose, fructose, lactose, high fructose corn syrup, honey, sugar alcohols (e.g., maltitol, erythritol, sorbitol), and combinations thereof.

Optional carbohydrates suitable for use herein also include soluble dietary fiber other than and in addition to the soluble, indigestible oligosaccharide component described herein, non-limiting examples of which include gum arabic, sodium carboxymethyl cellulose, guar gum, citrus pectin, low and high methoxy pectin, oat and barley glucans, carrageenan, psyllium and combinations thereof. Insoluble dietary fiber is also suitable as a carbohydrate source herein, non-limiting examples of which include oat hull fiber, pea hull fiber, soy hull fiber, soy cotyledon fiber, sugar beet fiber, cellulose, corn bran, and combinations thereof.

The nutritional compositions may therefore, and preferably, further comprise a carbohydrate component in addition to the dried fruit solids and the soluble indigestible oligosaccharide, wherein the dried fruit solids represents from about 3% to about 50%, including from about 5% to about 25%, by weigh of the total carbohydrate in the composition, and the soluble indigestible oligosaccharide represents from about 1% to about 20%, including from about 2% to about 5%, by weight of the total carbohydrates in the composition.

B) Protein

Optional proteins suitable for use in the nutritional compositions include hydrolyzed, partially hydrolyzed or non-hydrolyzed proteins or protein sources, and can be derived from any known or otherwise suitable source such as milk (e.g., casein, whey), animal (e.g., meat, fish, egg albumen), cereal (e.g., rice, corn), vegetable (e.g., soy, pea, potato), or combinations thereof. The proteins for use herein can also include, or be entirely or partially replaced by, free amino acids known for use in nutritional products, non-limiting examples of which include tryptophan, glutamine, tyrosine, L-methionine, cysteine, taurine, L-arginine, carnitine, and combinations thereof.

The nutritional compositions of the present invention preferably comprise a soy protein component, sources of which include, but are not limited to, soy flakes, soy protein isolates, soy protein concentrate, hydrolyzed soy protein, soy flour, soy protein fiber, or any other protein or protein source derived from soy. Commercial sources of soy protein are well known in the nutrition art, some non-limiting examples of which include soy protein isolates distributed by The Solae Company under the trade designation "Soy Protein Isolate EXP-H0118," "EXP-E-0101, and "Supro Plus 675."

The option soy protein component may represent from zero to 100%, preferably from about 20% to about 100%, more preferably from about 50% to 100%, including from about 75% to about 95%, and also including from about 80% to about 91%, of the total protein calories in the composition.

C) Lipid

Optional lipids suitable for use in the nutritional compositions include coconut oil, fractionated coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, faxseed oil, borage oil, cottonseed oils, evening primrose oil blackcurrant seed oil, transgenic oil sources, fungal oils, marine oils (e.g., tuna, sardine) and so forth.

The nutritional compositions of the present invention preferably comprise a flaxseed component, non-limiting examples of which include ground flaxseed and flaxseed oil. Ground flaxseed is preferred. Non limiting examples of flaxseed include red flaxseed, golden flaxseed, and combinations thereof. Golden flaxseed is preferred. Commercial sources of flaxseed are well known in the nutrition and formulation arts, some non-limiting examples of which include flaxseed and flax products available from the Flax Council of Canada, the Flax Consortium of Canada, and Heintzman Farms (North Dakota) (Dakota Flax Gold brand).

Other Optional Ingredients

The nutritional compositions of the present invention may further comprise other optional components that may modify the physical, chemical, aesthetic or processing characteristics of the products or serve as pharmaceutical or additional nutritional components when used in the targeted population. Many such optional ingredients are known or otherwise suitable for use in nutritional products or pharmaceutical dosage forms and may also be used in the compositions herein, provided that such optional ingredients are safe and effective for oral administration and are compatible with the essential and other selected ingredients in composition.

Non-limiting examples of such other optional ingredients include preservatives, anti-oxidants, buffers, additional pharmaceutical actives, sweeteners including artificial sweeteners (e.g., saccharine, aspartame, acesulfame K, sucralose) colorants, flavors, flavor enhancers, thickening agents and stabilizers, emulsifying agents, lubricants, and so forth.

The nutritional compositions of the present invention preferably comprise one or more minerals, non-limiting examples of which include phosphorus, sodium, chloride, magnesium, manganese, iron, copper, zinc, iodine, calcium, potassium, chromium, molybdenum, selenium, and combinations thereof. Calcium is preferred.

The nutritional compositions also preferably comprise one or more vitamins, non-limiting examples of which include carotenoids (e.g., beta-carotene, zeaxanthin, lutein, lycopene), biotin, choline, inositol, folic acid, pantothenic acid, choline, vitamin A, thiamine (vitamin $B_1$), riboflavin (vitamin $B_2$), niacin (vitamin $B_3$), pyridoxine (vitamin $B_6$), cyanocobalamine (vitamin $B_{12}$), ascorbic acid (vitamin C), vitamin D, vitamin E, vitamin K, and various salts, esters or other derivatives thereof, and combinations thereof.

The nutritional compositions of the present invention preferably comprise both vitamins and minerals.

Method of Use

A) Osteoporosis

The methods of the present invention are directed to the nutritional compositions described herein. These methods include the oral administration of such compositions to treat or prevent osteoporosis in individuals. The individual preferably consumes one serving of the nutritional composition daily. The serving is preferably administered as a single, undivided, daily dose, although the serving may also be divided into two or more partial or divided servings to be taken at two or more times during the day. The methods of the present invention include continuous daily administration as well as periodic or limited administration, although continuous daily administration is preferred. The methods of the present invention are preferably applied on a daily basis, wherein the daily administration is maintained continuously for at least 6 months, preferably for at least about 18-24 months, more preferably as a long term, continuous, daily, dietary supplement.

It is should be emphasized that the methods of the present invention as described herein are also intended to include the use of such methods in individuals unaffected by or not otherwise afflicted with osteoporosis or other bone-related disease or condition, for the purpose of preventing, minimizing, or delaying the development of such disease or condition over time. For such prevention purposes, the methods of the present invention preferably include continuous, daily administration of the compositions as described herein. Such preventive methods are preferably directed at women or others who are at risk of developing osteoporosis over time, especially females from 9-18 years of age.

The methods of the present invention include those embodiments directed to the treatment or prevention of osteoporosis, by which is meant that the methods are used in individuals afflicted by or otherwise at risk of developing osteoporosis, and means any method of affecting bone mineral density in an individual, which includes increasing bone mineral density, slowing the rate or onset of bone mineral density reduction, maintaining current bone mineral density, or reversing some or all of bone mineral density reductions or insufficiencies in individuals otherwise afflicted with osteoporosis.

The present invention also includes those embodiments directed to methods of 1) increasing bone strength, 2) reducing or attenuating bone loss, 3) reducing the risk of bone fracture associated with osteoporosis, and 4) reducing the risk of subsequent bone fracture associated with osteoporosis, all which are directed to the oral administration of the compositions described herein in the manner also described herein.

The methods directed to the reduction or attenuation of bone loss are defined herein as methods of decreasing the relative rate of bone resorption versus the rate of bone formation (which may result from an increase in the rate of bone formation, a decrease in the rate of bone resorption or both), increasing the rate or extent of mineralization within the bone, decreasing osteoclast activity or decreasing osteoclast number, or increasing osteoblast activity or increasing osteoblast number, or combinations thereof.

The term "bone mineral density" as used herein, unless otherwise specified, refers to the conventional use of the term in the nutrition or medical arts as an objective measurement of osteopenia or osteoporosis with respect to a healthy young woman's "normal" value. Such determination is often done by dual energy x-ray absorptiometry or DEXA. Bone mineral density from the hip is believed to be the most accurate for predicting risk of fracture, and that of the lumbar spine is considered to be best for monitoring treatment. The World Health Organization ("WHO") has defined acceptable bone mineral density as falling within one standard deviation of the "normal" value, or a T score above −1. Continued osteopenia can result in osteoporosis. The WHO has defined osteopenia as a value falling between 1 and 2.5 standard deviations, or a T score from −1 to −2.5, and has defined osteoporosis as bone mineral density less than 2.5 standard deviations from the "normal" value, or a T score of below −2.5. The National Osteoporosis Foundation has recommended treatment of osteoporosis for T scores below −2.5, and treatment of osteopenia for T scores below −1.5 with any risk factors present.

The term "osteopenia" as used herein, unless otherwise specified, is embodied by the term "osteoporosis" as also defined herein. The term "osteoporosis" as used herein, unless otherwise specified, is defined broadly to include any decrease or reduction in bone density by any defined or undefined cause or condition. Among the defined causes or conditions to which the methods of the present invention are directed include primary osteoporosis associated with menopause (natural, premature, or surgical), aging, or both, as well as secondary osteoporosis associated with medical conditions such as Paget's, chronic renal disease, amenorrhea from eating disorders, transplantation, hyperthyroidism, parathyroidism, or the use of certain medications, such as various cancer chemotherapies, gonadotropin releasing hormone agonists, medroxy progesterone acetate for birth control, corticosteroids, anticonvulsants, and others. The methods of the present invention are especially useful in younger individuals, especially those from age 10-18, including younger females from age 12-18, to help achieve peak bone mineral content and bone mineral density, for long term bone health benefits.

The methods of the present invention may be directed to the compositions described herein, wherein the individual preferably consumes at least about 1 g, more preferably from about 1 g to about 35 g, even more preferably from about 4 g to about 30 g, including from about 7 g to about 25 g, and also including from about 8 g to about 15 g, of the soluble, indigestible oligosaccharide per day; and wherein the individual also preferably consumes at least about 1 g, more preferably from about 20 g to about 80 g, even more preferably from about 25 g to about 70 g, and also including from about 30 g to about 50 g, of the dried fruit solids per day. Preferred are methods directed to the use of FOS, dried plum solids, or combinations thereof. More preferred are combinations of FOS and dried plum solids.

The methods of the present invention may also include the oral administration of those preferred embodiments of the present invention further comprising soy protein, wherein the individual preferably consumes at least about 1 g of the soy protein, preferably from about 1 g to about 160 g, including from about 3 g to about 100 g, and also including from about 6 g to about 60 g, of the soy protein, all on a per day basis.

The methods of the present invention also include the oral administration of those preferred embodiments of the present invention further comprising flaxseed, wherein the individual preferably consumes at least about 1 g of the flaxseed, more preferably from about 1 g to about 50 g, including from about 2 g to about 40 g, and also including from about 5 g to about 15 g, of the flaxseed, all on a per day basis.

B) Weight Control

The present invention includes those embodiments directed to methods for controlling body weight in estrogen-insufficient women by administration of the nutritional compositions described herein. The compositions may be administered as needed for controlling body weight, which most typically involves administration of the composition one or more times daily as a replacement for other foods. Total daily caloric intake should therefore be maintained or reduced so that the composition is not consumed in addition to an individual's normal or routine caloric intake.

The term "controlling body weight" as used herein, unless otherwise specified, means to target and control the weight of an individual to within a medically acceptable range for that individual, taking into account the individuals age, height, preexisting medical conditions, and so forth. A weight that is specific for the individual where their laboratory values used to assess a preexisting medical condition are in the normal range or a Body Mass Index (BMI) that is associated with a low-risk of developing a weight-related illness, such as type 2 diabetes, hypertension, hyperlipidemia, hypercholesterolemia or heart disease, for example, below about 25 or a waist circumference of less than about 40 for men and or less than about 35 for women, or a maintenance of weight for at least one year.

This particular embodiment of the present invention—controlling body weight in estrogen-insufficient women—may therefore include a method for maintaining weight and thus avoiding weight gain as well as a method for losing weight, depending upon the medical needs of the individual.

Method of Manufacture

The nutritional compositions for use herein may be prepared by any known or otherwise effective manufacturing technique for preparing the selected product form. Many such techniques are known for any given product form such as nutritional liquids or nutritional bars and can easily be applied by one of ordinary skill in the nutrition and formulation arts to the nutritional products described herein.

The non-dietary compositions for use herein can likewise be prepared by any known or otherwise effective manufacturing technique for preparing the selected product form. Many such techniques are well known, for example in the pharmaceutical industry, and can be applied by one of ordinary skill in the nutrition and formulation arts to product forms such as capsules, tablets, caplets, pills, liquids (e.g., suspensions, emulsions, gels, solutions), and so forth, and can easily be applied by one of ordinary skill in those arts to the non-dietary products described herein. As described herein, non-dietary products are those nutritional compositions of the present invention that are not dietary products as also defined herein. Liquid, milk or soy-based nutritional liquids, for example, may be prepared by first forming an oil and fiber blend containing all formulation oils, any emulsifier, fiber and fat-soluble vitamins. Additional slurries (typically a carbohydrate and two protein slurries) are prepared separately by mixing the carbohydrate and minerals together and the protein in water. The slurries are then mixed together with the oil blend. The resulting mixture is homogenized, heat processed, standardized with any water-soluble vitamins, flavored and the liquid terminally sterilized or aseptically filled or dried to produce a powder.

Other product forms such nutritional bars may be manufactured, for example, using cold extrusion technology as is known and commonly described in the bar manufacturing art. To prepare such compositions, typically all of the powdered components are dry blended together, which typically includes any proteins, vitamin premixes, certain carbohydrates, and so forth. The fat-soluble components are then blended together and mixed with any powdered premixes. Finally any liquid components are then mixed into the composition, forming a plastic like composition or dough. The resulting plastic mass can then be shaped, without further physical or chemical changes occurring, by cold forming or extrusion, wherein the plastic mass is forced at relatively low pressure through a die, which confers the desired shape. The resultant exudate is then cut off at an appropriate position to give products of the desired weight. If desired the solid product is then coated, to enhance palatability, and packaged for distribution.

The solid nutritional embodiments for use herein may also be manufactured through a baked application or heated extrusion to produce solid product forms such as cereals, cookies, crackers, and similar other product forms. One knowledgeable in the nutrition manufacturing arts is able to select one of the many known or otherwise available manufacturing processes to produce the desired final product.

The compositions described herein may, of course, be manufactured by other known or otherwise suitable techniques not specifically described herein without departing from the spirit and scope of the present invention. The present embodiments are, therefore, to be considered in all respects as illustrative and not restrictive and that all changes and equivalents also come within the description of the present invention. The following non-limiting examples further illustrate the compositions and methods of the present invention.

Experiment I

The purpose of this experiment was to evaluate the effects of various dietary ingredients on reversing the progression of osteopenia in a defined animal model. The animals in the study included estrogen-deficient, ovariectomized, osteopenia-induced, female rats (OVX) compared to a sham/control group (SHAM), all of which were orally administered nutritional compositions comprising different combinations of soy protein isolate, dried plum powder, FOS, and faxseed.

The study was a randomized, prospective, single-blind, positive controlled, parallel study. Animals (female rats) were either Sham operated or ovariectomized for the purpose of inducing osteopenia prior to administration of the test compositions. Control groups (Groups 1 and 2) were fed a casein-based diet while the treatment groups (Groups 3-7) were various combinations of 22% soy protein isolate, 7.5% dried plum powder, 5.0% fructooligosaccharides (FOS), or 7.5% flaxseed, all by weight of the composition being fed. Administration of the test compositions began after day 46 following surgical removal of the ovaries to assure the presence of an estrogen-deficient osteopenia in the OVX animal model.

Eighty-four, ninety day old Harlan Sprague-Dawley, 210 gm, female rats were purchased from Harlan Sprague Dawley Inc. (Indianapolis, Ind.). Upon arrival at the institution, rats were individually housed in stainless steel wire mesh cages in an environmentally controlled animal laboratory at 25° C. with a 12 hour light-ark cycle. The rats had free access to deionized water and semi-purified diets. They were handled according to National Institutes of Health guidelines for human treatment of experimental animals. They were observed for five days prior to the study for signs of illness by the animal technician responsible for providing husbandry.

Semi-purified diets were prepared for each animal group. To ensure equivalency, the diets were assayed for carbohydrate, protein, fat, calcium and phosphorus content prior to the feeding protocol. The diets were isonitrogenous, isocaloric and equivalent in calcium and phosphorus content, and each contained 22% protein, 67% carbohydrate and 11% fat. The diets containing soy protein isolate also contained 2.3 mg isoflavone per gm of soy protein (Protein Technologies International, St. Louis, Mo.). Ingredient concentrations included 7.5% dried plum (California Prune Board, Pleasanton, Calif.), 5% fructooligosaccharides (NutraFlora®, FOS Golden Technologies, Inc.), and 7.5% ground flaxseed. Diets were stored at 5° C. From days 6-46, food consumption data were collected. SHAM animals were fed ad libitum and their precise food intakes were measured every three days. Before each feeding, the remaining food was weighed and the amount ingested was calculated. Rats in the other groups were pair-fed to the mean intake of the sham animals and had free access to deionized water. OVX animals (Groups 2-7) were ovarian hormone/estrogen deficient, i.e., ovaries surgically removed.

| | Experiment I - Study Groups, Diets* | | | | | | |
|---|---|---|---|---|---|---|---|
| Ingredients | Group 1 SHAM Casein diet (control) | Group 2 OVX Casein diet (control) | Group 3 OVX Soy diet | Group 4 OVX Soy diet + plum | Group 5 OVX Soy diet + FOS | Group 6 OVX Soy diet + FOS + plum | Group 7 OVX Soy diet + FOS + plum + flaxseed |
| Casein | 227 | 227 | — | — | — | — | — |
| Soy Protein Isolate | — | — | 227 | 224.75 | 224.75 | 224.75 | 208.6 |
| Dried Plum | — | — | — | 75 | — | 75 | 75 |
| Flaxseed | — | — | — | — | — | — | 75 |
| FOS | — | — | — | — | 50 | 50 | 50 |
| Sucrose | 417 | 417 | 417.5 | 417.5 | 417.5 | 417.5 | 417.5 |
| Cornstarch | 200 | 200 | 200 | 140 | 150 | 90 | 60 |
| Cellulose | 56 | 56 | 56 | 49.25 | 56 | 49.25 | 39.96 |
| Canola oil | 57 | 57 | 57 | 56.6 | 57 | 56.6 | 37.6 |
| Vitamin Mixture | 10 | 10 | 10 | 10 | 10 | 10 | 10 |
| Mineral Mixture | 13.4 | 13.4 | 13.4 | 13.4 | 13.4 | 13.4 | 13.4 |
| Calcium Carbonate | 10 | 10 | 10 | 9.86 | 10 | 9.86 | 9.45 |
| Sodium phosphate monobasic | 3.9 | 3.9 | 3.9 | 3.72 | 3.72 | 3.72 | 3.72 |
| Potassium phosphate monobasic | 2.4 | 2.4 | 2.4 | 2.22 | 2.4 | 2.22 | 2.22 |
| Potassium citrate monohydrate | 0.9 | 0.9 | 0.9 | 0.9 | 0.9 | 0.9 | 0.9 |
| Choline bitartrate | 2.5 | 2.5 | 2.5 | 2.5 | 2.5 | 2.5 | 2.5 |
| L-cysteine | 1.8 | 1.8 | 1.8 | 1.8 | 1.8 | 1.8 | 1.8 |

*amounts listed as gm per kg of diet

Treatment effectiveness was evaluated as between the control groups (Groups 1 and 2) and the treatment groups (Groups 3-7) by measuring and comparing their respective changes over the course of the study in bone mineral density (whole body, femur, spine), bone strength, bone mineral content (whole body, femur, spine), biochemical markers of bone turnover, and bone histomorphometry.

| | Experiment I - Summary of Results[1] | | | |
|---|---|---|---|---|
| | Group 1 Sham Casein diet (control) | Group 2 OVX Casein diet (control) | Group 3 OVX Soy diet | Group 4 OVX Soy diet + plum |
| Bone mineral density | | | | |
| Whole | $0.1724 \pm 0.0014^D$ | $0.1598 \pm 0.0012^A$ | $0.1614 \pm 0.0010^{AB}$ | $0.1653 \pm 0.0015^{ABC}$ |
| Femur | $0.2507 \pm 0.0029^C$ | $0.2262 \pm 0.0031^A$ | $0.2329 \pm 0.0018^{AB}$ | $0.2355 \pm 0.0035^{AB}$ |
| Spine | $0.2462 \pm 0.0032^C$ | $0.2150 \pm 0.0039^A$ | $0.2197 \pm 0.0026^{AB}$ | $0.2225 \pm 0.0043^{AB}$ |
| Bone mineral content (LS Mean) | | | | |
| Whole body | $10.9523^D$ | $10.1304^A$ | $10.2520^{AB}$ | $10.4936^{ABC}$ |
| Femur | $0.4828^C$ | $0.4336^A$ | $0.4522^{AB}$ | $0.4535^{AB}$ |
| Spine | $0.1505^C$ | $0.1328^A$ | $0.1356^{AB}$ | $0.1357^{AB}$ |
| Left Femur Ultimate Load (N) | $124.6 \pm 2.2$ | $119.5 \pm 3.0$ | $120.0 \pm 1.6$ | $123.5 \pm 2.8$ |

-continued

| Experiment I - Summary of Results[1] | | | | |
|---|---|---|---|---|
| Urinary Deoxy pyridinoline | $39.94 \pm 8.92^A$ | $98.87 \pm 25.75^B$ | $57.07 \pm 3.71^{AB}$ | $66.92 \pm 17.75^{AB}$ |
| Weight Gain during Treatment period | $12.4 \pm 2.3$ | $11.4 \pm 3.3$ | $10.8 \pm 4.1$ | $3.5 \pm 3.4$ |

| | Group 5 OVX Soy diet + FOS | Group 6 OVX Soy diet + FOS + plum | Group 7 OVX Soy diet + FOS + plum + flaxseed |
|---|---|---|---|
| Bone mineral density | | | |
| Whole | $0.1672 \pm 0.0014^{BCD}$ | $0.1675 \pm 0.0018^{CD}$ | $0.1661 \pm 0.0012^{BC}$ |
| Femur | $0.2382 \pm 0.0017^B$ | $0.2375 \pm 0.0020^B$ | $0.2389 \pm 0.0016^B$ |
| Spine | $0.2281 \pm 0.0035^{AB}$ | $0.2323 \pm 0.0019^{BC}$ | $0.2273 \pm 0.0025^{AB}$ |
| Bone mineral content (LS Mean) | | | |
| Whole body | $10.6106^{BCD}$ | $10.6329^{CD}$ | $10.5504^{BCD}$ |
| Femur | $0.4544^B$ | $0.4558^B$ | $0.4564^B$ |
| Spine | $0.1389^{AB}$ | $0.1425^{BC}$ | $0.1386^{AB}$ |
| Left Femur Ultimate Load (N) | $129.6 \pm 3.1$ | $125.1 \pm 2.1$ | $129.1 \pm 2.8$ |
| Urinary Deoxy pyridinoline | $48.04 \pm 3.22^{AB}$ | $54.22 \pm 3.09^{AB}$ | $52.66 \pm 7.49^{AB}$ |
| Weight Gain during Treatment period | $6.8 \pm 2.7$ | $5.4 \pm 3.8$ | $3.6 \pm 2.8$ |

[1]Significant findings for the feeding groups were examined with Tukey's HSD test to determine where statistical differences occur (C > B > A). Tukey's HSD is used as a most conservative test benchmark for comparing all treatment group comparisons for each variable analyzed Bone Mineral Density (BMD)

ANOVA (One-Way Analysis of Variance) detected a significant treatment effect where whole body BMD was significantly higher for all treated groups, except for soy alone as compared to OVX-casein (p=0.0003). There was a significant difference in whole body BMD between SHAM and OVX-casein groups (p<0.0001, SHAM>OVX). Whole body BMD was not significantly different with treatment soy+plum+FOS compared to SHAM. All other treatments, however, were significantly lower than SHAM. ANOVA detected an ingredient effect to increase whole body BMD in treatments with FOS compared to treatments without FOS (p=0.0054). Tukey's test also showed that whole body BMD for the soy+plum+FOS combination treated group was significantly higher than for the group treated with soy alone (p=0.0360).

ANOVA detected a significant treatment effect where femur BMD was significantly higher for all treatment groups compared to OVX-Casein except for treatment with soy alone (p=0.0045). There was a significant difference in femur BMD between SHAM and OVX-Casein (p<0.0001, SHAM>OVX). Femur BMD was significantly lower for all treatments compared to SHAM (p<0.0001).

ANOVA detected a significant treatment effect where lumbar spine BMD was significantly higher for all treatment groups compared to OVX-Casein except for treatments with soy and soy+plum (p=0.0048). There was a significant difference in spine BMD between SHAM and OVX-casein (p<0.0001, SHAM>OVX). ANOVA detected an ingredient effect to increase lumbar spine BMD in treatments with FOS compared to treatments without FOS (p=0.0046). Lumbar spine BMD was significantly lower for all treatments compared to SHAM (p<0.0001).

Bone Mineral Content (BMC)

ANOVA detected a significant treatment effect where whole body BMC was significantly greater for all treatment groups, except for soy alone, compared to OVX-casein (p=0.0003). There was a significant difference in whole body BMC between SHAM and OVX-casein groups (p<0.0001, SHAM>OVX). Whole body BMC for treatments containing soy+FOS or soy+plum+FOS were not significantly different compared to SHAM. Whole body BMC was significantly lower, however, for all the other treatments compared to SHAM (p=0.0002). Tukey's test also showed that whole body BMC for the group treated with the soy+plum+FOS combination is significantly greater than for the group treated with soy alone (p=0.0359).

ANOVA detected a significant treatment effect where femur BMC was significantly higher for all treatment groups compared to OVX-casein (p=0.0092). There was a significant difference in femur BMC between SHAM and OVX-Casein (p<0.0001, SHAM>OVX). Femur BMC was significantly lower for all treatments compared to SHAM (p<0.0001).

ANOVA detected a significant treatment effect where lumbar spine BMC was significantly higher for the group treated with soy+plum+FOS as compared to OVX-casein (p=0.0027). There was a significant difference in spine BMC between SHAM and OVX-casein (p<0.0001, SHAM>OVX). ANOVA detected an ingredient effect to increase lumbar spine BMC in treatments with FOS compared to treatments without FOS (p=0.0067). Lumbar spine BMC was significantly lower for all treatments compared to SHAM (p<0.0001).

Discussion

Although soy alone did not reverse osteopenia in the test animals, osteopenia was reversed in those groups administered soy in combination with plum, FOS or flaxseed. As expected, ovariectomy induced osteopenia in the whole body, femur and spine. Soy administration alone was unable to sufficiently restore bone mineral density beyond levels of OVX-casein animals. Bone mineral density of the whole body, femur and lumbar spine were statistically significantly higher with the soy combinations as compared to OVX-casein. Likewise, bone mineral content of the whole body and spine was also greater for groups treated with a soy combination compared to casein.

A comparison among treatments showed that soy+plum+FOS was more effective than soy alone to increase whole body BMC. These increases in whole body BMC of animals treated with soy+FOS or soy+plum+FOS reached levels that were not statistically different from SHAM levels. Percent ash of the lumbar spine was also significantly increased due to soy+plum+FOS.

FOS had a significant effect to increase whole body and lumbar spine BMC and lumbar spine BMD.

The results of this study have shown that select combinations of bone bioactive ingredients have a greater effect in reversing bone loss than either of their component ingredients when used alone. Unlike certain of the bioactive combinations tested, neither soy protein isolate compositions (as the only bone bioactive ingredient) nor casein protein compositions were able to reverse established osteopenia in the ovariectomized rat model of postmenopausal osteoporosis.

All soy combinations were able to increase whole body, femur and spine BMD above ovariectomized casein controls (except soy+plum for spine). The combination of soy+plum+FOS was particularly effective in increasing whole body BMD to levels not significantly different from those observed in the SHAM group. This combination, as well as soy+FOS, was also able to increase whole body BMC to levels not significantly different from the SHAM group. Spine BMD and BMC and percent ash weight were all significantly higher in the soy+plum+FOS treatment group mainly due to the effect of FOS since treatments with FOS had significantly higher spine BMD and BMC values compared to treatments that did not contain FOS. The ability of an agent to be strong enough to reverse bone loss in the spine is especially desirous because the effect of estrogen deficiency on bone loss from the spine (cancerous bone) is greater and occurs earlier than bone loss from the femur (cortical).

Femoral bone strength was increased by treatment with soy+FOS and especially soy+plum+FOS+flaxseed. This suggests that increases of bone mineral density in response to the soy combinations is also accompanied by good quality bones.

Bone turnover, which is accelerated in estrogen deficiency, was significantly reduced with treatments containing soy+plum+FOS and soy+plum+FOS+flaxseed as reflected in decreases in biochemical bone markers and bone histomorphometrical parameters. Reductions in bone turnover is a mechanism of many anti-resorptive drugs.

SUMMARY

This study demonstrated that soy, dried plum, FOS and flaxseed combinations reverse the consequences of estrogen deficiency, i.e., osteopenia or osteoporosis, decreased bone strength, accelerated bone turnover, accelerated bone resorption. Preferred were combinations of 1) soy protein isolate+dried plum powder+FOS+flaxseed and 2) soy protein isolate+dried plum+FOS.

Experiment II

The purpose of this second experiment was to duplicate the results of Experiment I for animals treated with soy protein isolate+dried plum powder+FOS on the reversal of bone loss due to ovarian hormone deficiency. The study was a randomized, prospective, single-blind, positive controlled, parallel study. The animals in the study included estrogen-deficient, ovariectomized, osteopenia-induced, female rats (OVX) compared to a sham group (SHAM).

As shown in the following table, the control groups, including the sham group, were fed a casein-based diet, while treatment groups were fed diets containing casein, or soy, fructooligosaccharides, dried plum powder or green tea catechins. As in the first experiment, administration of the test compositions began after day 46 following surgical removal of the ovaries to assure the presence of an estrogen-deficient osteopenia in the OVX animal model.

The study was a randomized, prospective, single-blind, positive controlled, parallel study. Animals (female rats) were either Sham operated or ovariectomized for the purpose of inducing osteopenia prior to administration of the test compositions. Control groups (Groups 1 and 2) were fed a casein-based diet while the treatment groups (Groups 3-7) were fed various combinations of 22% soy protein isolate, 7.5% dried plum powder, 5.0% fructooligosaccharides (FOS), or 7.5% flaxseed, all by weight of the composition being fed.

Eighty, (n=10/group) ninety day old Harlan Sprague-Dawley, 210 gm, female rats were purchased from Harlan Sprague Dawley Inc. (Indianapolis, Ind.). Upon arrival at the institution, rats were individually housed in stainless steel wire mesh cages in an environmentally controlled animal laboratory at 25° C. with a 12 h light-dark cycle. The rats had free excess to deionized water and semi-purified diets. They were handled according to National Institutes of Health guidelines for humane treatment of experimental animals. They were observed for five days prior to the study for signs of illness by the animal technician responsible for providing husbandry.

The semi-purified animal diets are described in the following table. To ensure equivalency, the diets were assayed for carbohydrate, protein, fat, calcium and phosphorus content prior to the feeding protocol. All diets were isonitrogenous, isocaloric and equivalent in calcium and phosphorus content. The diets each contained 22% protein, 67% carbohydrate and 11% fat. The protein sources for the treatment diets contained either soy protein isolate which contained 2.3 mg total isoflavone/gm soy protein (Protein Technologies International, St. Louis, Mo.), or casein. The treatment diets contained various combinations of 7.5% dried plum (Sunsweet Growers, Inc., Pleasanton, Calif.), 5% fructooligosaccharides (Nutra-Flora®, FOS Golden Technologies, Inc.), and 0.2% green tea catechins (P. L. Thomas). Diets were stored at 5° C. From days 6-46, food consumption data was collected. Sham animals were fed ad libitum and their precise food intakes were measured every three days. Before each feeding, the food remaining was weighed and the amount ingested was calculated. Rats in the other groups were pair-fed to the mean intake of the sham animals and had free access to deionized water. OVX animals (Groups 2-8) were ovarian hormone/estrogen deficient, i.e., ovaries surgically removed.

| Diet Ingredients | Group 1 SHAM Casein diet (control) | Group 2 OVX Casein diet (control) | Group 3 OVX Soy diet + FOS + Plum | Group 4 OVX Casein diet + Plum | Group 5 OVX Casein diet + FOS + Plum | Group 6 OVX Casein diet + FOS + green tea | Group 7 OVX Casein diet + FOS | Group 8 OVX Casein diet + FOS + green tea + plum |
|---|---|---|---|---|---|---|---|---|
| Casein | 227 | 227 | — | 22475 | 224.75 | 227 | 227 | 224.75 |
| Soy Protein Isolate | — | — | 224.75 | — | — | — | — | — |
| Dried Plum | — | — | 75 | 75 | 75 | — | — | 75 |
| Green Tea Catechins | — | — | — | — | — | 2.0 | — | 2 |
| FOS | — | — | 50 | — | 50 | 50 | 50 | 50 |
| Sucrose | 417 | 417 | 417.5 | 417 | 417.5 | 417 | 417 | 417.5 |
| Cornstarch | 200 | 200 | 90 | 140 | 90 | 150 | 150 | 90 |
| Cellulose | 56 | 56 | 49.25 | 49.25 | 49.25 | 56 | 56 | 49.25 |
| Canola oil | 57 | 57 | 56.6 | 56.6 | 56.6 | 57 | 57 | 56.6 |
| Vitamin Mixture | 10 | 10 | 10 | 10 | 10 | 10 | 10 | 10 |
| Mineral Mixture | 13.4 | 13.4 | 13.4 | 13.4 | 13.4 | 13.4 | 13.4 | 13.4 |
| Calcium Carbonate | 10 | 10 | 9.86 | 9.86 | 9.86 | 10 | 10 | 9.86 |
| Sodium phosphate monobasic | 3.9 | 3.9 | 3.72 | 3.72 | 3.72 | 3.9 | 3.9 | — |
| Potassium phosphate monobasic | 2.4 | 2.4 | 2.22 | 2.22 | 2.22 | 2.40 | 2.40 | 2.22 |
| Potassium citrate monohydrate | 0.9 | 0.9 | 0.9 | 0.9 | 0.9 | 0.9 | 0.9 | 0.9 |
| Choline bitartrate | 2.5 | 2.5 | 2.5 | 2.5 | 2.5 | 2.5 | 2.5 | 2.5 |
| L-cysteine | 1.8 | 1.8 | 1.8 | 1.8 | 1.8 | 1.8 | 1.8 | 1.8 |

*amounts listed are gm per kg of diet

Treatment effectiveness was evaluated as between the control groups (Groups 1 and 2) and the treatment groups (Groups 3-7) by measuring and comparing their respective changes over the course of the study in bone mineral density, bone mineral content (bone calcium and phosphorus content), and micro-computed tomography.

| Experiment II - Summary of Results[1] | Group 1 SHAM Casein diet | Group 2 OVX Casein diet | Group 3 OVX Soy diet + FOS + Plum | Group 4 OVX Casein diet + Plum |
|---|---|---|---|---|
| Bone mineral density (Mean ± SE) | | | | |
| Whole body | $0.169 \pm 0.001^C$ | $0.161 \pm 0.002^A$ | $0.168 \pm 0.001^{BC}$ | $0.162 \pm 0.001^A$ |
| Femur | $0.245 \pm 0.002^B$ | $0.226 \pm 0.003^A$ | $0.236 \pm 0.002^{AB}$ | $0.227 \pm 0.002^A$ |
| Spine | $0.242 \pm 0.003^C$ | $0.213 \pm 0.004^A$ | $0.230 \pm 0.003BC$ | $0.218 \pm 0.003^{AB}$ |
| Change in Bone mineral density (from OVX Baseline) | | | | |
| Whole body | — | 0.000 Baseline | — | 0.001 |
| Femur | — | 0.000 Baseline | — | 0.001 |
| Spine | — | 0.000 Baseline | — | 0.005 |
| Bone mineral content (LS Mean ± SE) | | | | |
| Whole body | $10.45 \pm 0.10^C$ | $9.91 \pm 0.09^A$ | $10.32 \pm 0.08^{BC}$ | $9.89 \pm 0.09^A$ |
| Femur | $0.4608 \pm 0.0038^C$ | $0.4176 \pm 0.0039^A$ | $0.4362 \pm 0.0037^B$ | $0.4215 \pm 0.0039^{AB}$ |
| Spine | $0.1390 \pm 0.0014^C$ | $0.1223 \pm 0.0015^A$ | $0.1318 \pm 0.0014^B$ | $0.1246 \pm 0.0015^A$ |

-continued

Experiment II - Summary of Results[1]

Bone Volume/Total Volume (Ranked) Mean ± SE

| | | | |
|---|---|---|---|
| 0.239 ± 0.25$^C$ | 0.080 ± 0.005$^A$ | 0.109 ± 0.005$^{BC}$ | 0.093 ± 0.004$^{AB}$ |

Trabecular No. (1/mm) (Ranked) Mean ± SE

| | | | |
|---|---|---|---|
| 4.69 ± 0.37$^C$ | 1.74 ± 0.09$^A$ | 2.38 ± 0.12$^{BC}$ | 2.08 ± 0.08$^{AB}$ |

Trabecular separation (mm) (Ranked) Mean + SE

| | | | |
|---|---|---|---|
| 0.234 ± 0.045$^C$ | 0.596 ± 0.035$^A$ | 0.432 ± 0.026$^{BC}$ | 0.490 ± 0.020$^{AB}$ |

Connective Density (Ranked) Mean ± SE

| | | | |
|---|---|---|---|
| 133.7 ± 16.6$^C$ | 18.4 ± 2.0$^A$ | 29.8 ± 2.2$^{BC}$ | 23.6 ± 1.1$^{AB}$ |

Structural Model Index (Ranked) Mean ± SE

| | | | |
|---|---|---|---|
| 1.422 ± 0.202$^A$ | 2.478 ± 0.049$^B$ | 2.375 ± 0.026$^{AB}$ | 2.355 ± 0.039$^{AB}$ |

| | | | | |
|---|---|---|---|---|
| Body Weight Gain during Treatment period Mean ± SE | 3.4 ± 2.1 | 9.3 ± 4.1 | 15.3 ± 2.8 | 15.2 ± 4.5 |

| | Group 5 OVX Casein diet + FOS + Plum | Group 6 OVX Casein diet + FOS + green tea | Group 7 OVX Casein diet + FOS | Group 8 OVX Casein diet + FOS + green tea/Plum |
|---|---|---|---|---|
| | Bone mineral density (Mean ± SE) | | | |
| Whole body | 0.166 ± 0.001$^{ABC}$ | 0.161 ± 0.001$^A$ | 0.162 ± 0.002$^{AB}$ | 0.161 ± 0.002$^A$ |
| Femur | 0.232 ± 0.002$^A$ | 0.225 ± 0.003$^A$ | 0.228 ± 0.003$^A$ | 0.228 ± 0.004$^A$ |
| Spine | 0.226 ± 0.003$^{AB}$ | 0.217 ± 0.002$^{AB}$ | 0.215 ± 0.004$^A$ | 0.215 ± 0.003$^A$ |
| | Change in Bone mineral density (from OVX Baseline) | | | |
| Whole body | 0.005 | — | 0.001 | — |
| Femur | 0.006 | — | 0.002 | — |
| Spine | 0.013 | — | 0.002 | — |
| | Bone mineral content (LS Mean ± SE) | | | |
| Whole body | 10.19 ± 0.09$^{ABC}$ | 9.90 ± 0.09$^A$ | 10.01 ± $^{AB}$ | 9.92 ± 0.09$^A$ |
| Femur | 0.4288 ± 0.0040$^{AB}$ | 0.4205 ± 0.0039$^{AB}$ | 0.4286 ± 0.0040$^{AB}$ | 0.4247 ± 0.0039 |
| Spine | 0.1279 ± 0.0015$^{AB}$ | 0.1241 ± 0.0015$^A$ | 0.1255 ± 0.0015$^{AB}$ | 0.1257 ± 0.0015$^{AB}$ |
| | Bone Volume/Total Volume (Ranked) Mean ± SE | | | |
| | 0.100 ± 0.003$^{ABC}$ | 0.088 ± 0.006$^{AB}$ | 0.107 ± 0.020$^{AB}$ | 0.082 ± 0.004$^A$ |
| | Trabecular No. (1/mm) (Ranked) Mean ± SE | | | |
| | 2.12 ± 0.09$^{AB}$ | 1.88 ± 0.11$^{AB}$ | 2.25 ± 0.31$^{AB}$ | 1.95 ± 0.10$^{AB}$ |
| | Trabecular separation (mm) (Ranked) Mean + SE | | | |
| | 0.489 ± 0.027$^{AB}$ | 0.549 ± 0.031$^{AB}$ | 0.0499 ± 0.047$^{AB}$ | 0.534 ± 0.031$^{AB}$ |
| | Connective Density (Ranked) Mean ± SE | | | |
| | 25.5 ± 1.4$^{AB}$ | 20.4 ± 2.4$^A$ | 33.8 ± 11.5$^{AB}$ | 21.1 ± 1.6$^{AB}$ |
| | Structural Model Index (Ranked) Mean ± SE | | | |
| | 2.350 ± 0.038$^{AB}$ | 2.441 ± 0.044$^B$ | 2.318 ± 0.138$^B$ | 2.458 ± 0.033$^B$ |
| Body Weight Gain during Treatment period Mean ± SE | 9.5 ± 2.6 | 8.6 ± 2.9 | 3.4 ± 3.0 | 9.0 ± 4.1 |

[1]Significant findings for the feeding groups were examined with Tukey's HSD test to determine where statistical differences occur (C > B > A). Tukey's HSD is used as a most conservative test benchmark for comparing all treatment group comparisons for each variable analyzed.

Bone Mineral Density (Whole Body)

The testing of the feeding effects and effects of ovariectomy surgery (OVX) on whole body BMD consisted of four separate analyses comparing measurements made from DEXA scans at study entry (Day 1), baseline (Day 46), end of study (Day 106) and also, to measure change occurring during the treatment feeding period, Day 106 adjusted for baseline (Day 46).

An ANOVA using Tukey's HSD test showed that no differences in whole body BMD exist between treatment groups at Day 1. By Day 46, however, an ANOVA using Tukey's HSD test detected a significant effect of ovariectomy with the SHAM-Casein group whole body BMD being significantly higher ($p=0.05$) than all the treatment groups of ovariectomized rats even though all groups were being fed the same casein diet during the period. During the treatment period (Day 46 to Day 106), the effect of ovariectomy on whole body BMD continued as a GLM contrast t-test showed that whole body BMD at Day 106 in the SHAM-Casein group was significantly higher than whole body BMD in the OVX-Casein group. A GLM contrast t-test of whole body BMD at Day 106 adjusted for whole body BMD at Day 46, however, detected no difference between the SHAM-Casein and OVX-Casein groups demonstrating that the significant effect of ovariectomy on change in whole body BMD must have occurred only during the pre-treatment (Day 1 to Day 46) period.

ANOVAs using Dunnett's test showed that whole body BMD at Day 106 in the OVX-Soy+FOS+Dried Plum group was significantly higher than the OVX-Casein, OVX-Casein+Dried Plum, OVX-Casein+FOS+Green Tea and OVX-Casein+FOS+Dried Plum+Green Tea groups but was not different from the OVX-Casein+FOS+Dried Plum group. Additionally, an ANOVA using Dunnett's test showed that whole body BMD at Day 106 for only the two treatments with the FOS+dried plum combination were not different from the SHAM-Casein group suggesting that adding the FOS+dried plum combination raises whole body BMD. GLM contrast t-tests demonstrated that whole body BMD in treatments with the FOS+dried plum combination were significantly higher than in treatments with neither FOS nor dried plum and in treatments with only dried plum suggesting that the combination effect is due mainly the effect of adding FOS than to the effect of adding dried plum.

GLM contrast t-tests of whole body BMD at Day 106 showed that there was no difference between the soy and casein protein sources, and that dried plum was superior to green tea as a polyphenol source added with FOS since dried plum alone was significantly higher than green tea alone and dried plum added alone was significantly higher than the dried plum+green tea combination.

Results from ANOVAs of whole body BMD at Day 106 adjusted for whole body BMD at Day 46 were consistent with the ANOVAs of just whole body BMD at Day 106.

Bone Mineral Density (Femur)

A GLM contrast t-test showed that femur BMD in the SHAM-Casein group was significantly higher than femur BMD in the OVX-Casein group. ANOVAs using Dunnett's test showed that femur BMD in the OVX-Soy+FOS+Dried Plum group was significantly higher than the OVX-Casein and OVX-Casein+FOS+Green Tea groups and was marginally higher ($0.05<p<0.10$) than the OVX-Casein+Dried Plum group but was not different from the OVX-Casein+FOS+Dried Plum, OVX-Casein+FOS and OVX-Casein+FOS+Dried Plum+Green Tea groups. Additionally, an ANOVA using Dunnett's test showed that femur BMD in the SHAM-Casein group was significantly higher than all the ovariectomized rat treatment groups. GLM contrast t-tests demonstrated that: femur BMD in treatments with the FOS+dried plum combination were marginally higher than in treatments with neither FOS nor dried plum; there was no difference in femur BMD between the soy and casein protein sources; and that dried plum was superior to green tea as a polyphenol source added with FOS since femur BMD with dried plum alone was significantly higher than green tea alone. The trends for femur BMD were consistent with the trends for whole body BMD and lumbar spine BMD but the results were not as strong.

Bone Mineral Density (L4 Lumbar Spine)

A GLM contrast t-test showed that lumbar spine BMD in the SHAM-Casein group was significantly higher than lumbar spine BMD in the OVX-Casein group. ANOVAs using Dunnett's test showed that lumbar spine BMD in the OVX-Soy+FOS+Dried Plum group was significantly higher than the OVX-Casein, OVX-Casein+Dried Plum, OVX-Casein+FOS+Green Tea, OVX-Casein+FOS and OVX-Casein+FOS+Dried Plum+Green Tea groups but was not different from the OVX-Casein+FOS+Dried Plum group. Additionally, an ANOVA using Dunnett's test showed that lumbar spine BMD in the SHAM-Casein group was significantly higher than all the ovariectomized rat treatment groups. GLM contrast t-tests demonstrated that lumbar spine BMD in treatments with the FOS+dried plum combination were significantly higher than in treatments with neither FOS nor dried plum and in treatments with FOS alone and was marginally higher than in treatments with dried plum alone. Additionally, lumbar spine in the OVX-Casein+FOS+Dried Plum group was significantly higher than the OVX-Casein groups strongly suggesting a FOS+dried plum combination effect more than an individual ingredient effect GLM contrast t-tests also showed that there was no difference in lumbar spine BMD between the soy and casein protein sources; and that dried plum was superior to green tea as a polyphenol source added with FOS since lumbar spine BMD with dried plum alone was marginally higher than green tea alone, dried plum alone was significantly higher than no dried plum and dried plum alone was significantly higher than for the dried plum+green tea combination. The trends for lumbar spine BMD were consistent with the trends for whole body BMD and femur BMD while the results, however, were not as strong as for whole body BMD but stronger than for femur BMD

Bone Mineral Content (Whole Body)

The testing of the feeding effects and effects of ovariectomy surgery on whole body BMC adjusted for area at time of DEXA scan consisted of three separate analyses comparing measurements made from DEXA scans at study entry (Day 1), baseline (Day 46), and end of study (Day 106).

An ANCOVA using Tukey's HSD test showed that no differences in whole body BMC exist between treatment groups at Day 1. By Day 46, however, an ANCOVA using Tukey's HSD test detected a significant effect of ovariectomy with the SHAM-Casein group whole body BMC being significantly higher than all the treatment groups of ovariectomized rats even though all groups were being fed the same casein diet during the period. During the treatment period (Day 46 to Day 106), the effect of ovariectomy on whole body BMC continued as a GLM contrast t-test showed that whole body BMC at Day 106 in the SHAM-Casein group was significantly higher than whole body BMC in the OVX-Casein group.

ANCOVAs using Dunnett's test showed that whole body BMC at Day 106 in the OVX-Soy+FOS+Dried Plum group was significantly higher than the OVX-Casein, OVX-Casein+Dried Plum, OVX-Casein+FOS, OVX-Casein+FOS+Green Tea and OVX-Casein+FOS+Dried Plum+Green Tea groups but was not different from the OVX-Casein+FOS+Dried Plum group. Additionally, an ANCOVA using Dunnett's test showed that whole body BMC at Day 106 for only the two treatments with the FOS+dried plum combination were not different from the SHAM-Casein group suggesting that adding the FOS+dried plum combination raises whole body BMC. GLM contrast t-tests demonstrated that whole body BMC in treatments with the FOS+dried plum combination were significantly higher than in treatments with neither FOS nor dried plum.

GLM contrast t-tests of whole body BMC at Day 106 showed that there was no difference between the soy and casein protein sources, and that dried plum was superior to green tea as a polyphenol source added with FOS since dried plum alone was significantly higher than green tea alone and dried plum added alone was significantly higher than the dried plum+green tea combination.

Bone Mineral Content (L4 Lumbar Spine)

A GLM contrast t-test showed that lumbar spine BMC in the SHAM-Casein group was significantly higher than lumbar spine BMC in the OVX-Casein group. ANCOVAs using Dunnett's test showed that lumbar spine BMC in the OVX-Soy+FOS+Dried Plum group was significantly higher than the OVX-Casein, OVX-Casein+Dried Plum, OVX-Casein+FOS+Green Tea, OVX-Casein+FOS and OVX-Casein+FOS+Dried Plum+Green Tea groups but was not different from the OVX-Casein+FOS+Dried Plum group. Additionally, an ANCOVA using Dunnett's test showed that lumbar spine BMC in the SHAM-Casein group was significantly higher than all the ovariectomized rat treatment groups. GLM contrast t-tests demonstrated that lumbar spine BMC in treatments with the FOS+dried plum combination were significantly higher than in treatments with neither FOS nor dried plum, thus suggesting a combination effect above a single ingredient effect; there was no difference in lumbar spine BMC between the soy and casein protein sources; and that dried plum was superior to green tea as a polyphenol source added with FOS since lumbar spine BMC with dried plum alone was marginally higher than green tea alone. The trends for lumbar spine BMC were largely consistent with the trends for whole body BMC and femur BMC while the results, however, were not as strong as for whole body BMC but stronger than for femur BMC.

Bone Volume Per Total Volume

A GLM contrast t-test showed that ranked bone volume per total volume (BV/TV) in the SHAM-Casein group was significantly higher than ranked BV/TV in the OVX-Casein group. ANOVAs using Dunnett's test showed that ranked BV/TV in the OVX-Soy+FOS+Dried Plum group was significantly higher than the OVX-Casein, OVX-Casein+FOS+Green Tea and OVX-casein+FOS+Dried Plum+Green Tea groups but was not different from the OVX-Casein+FOS+Dried Plum, OVX-Casein+FOS and OVX-Casein+Dried Plum groups. Additionally, an ANOVA using Dunnett's test showed that ranked BV/TV in the SHAM-Casein group was significantly higher than all the ovariectomized rat treatment groups except the OVX-Soy+FOS+Dried Plum group. GLM contrast t-tests demonstrated that: ranked BV/TV for both dried plum alone and FOS alone was marginally higher than with no dried plum or no FOS, while ranked BV/TV with the FOS+dried plum combination was significantly higher than in treatments with neither FOS nor dried plum but was not different from FOS alone or dried plum alone suggesting that there are individual ingredients effects but not an added combination effect; there was no difference in ranked BV/TV between the soy and casein protein sources; and that, for ranked BV/TV, dried plum was superior to green tea as a polyphenol source added with FOS since dried plum alone was significantly higher than green tea alone and dried plum alone was significantly higher than the dried plum+green tea combination.

Trabecular Number, Trabecular Separation, Trabecular Thickness

GLM contrast t-tests showed that ranked trabecular number and trabecular separation in the SHAM-Casein group were significantly higher than ranked trabecular number and trabecular separation in the OVX-casein group although this difference was not seen for ranked trabecular thickness. ANOVAs using Dunnett's test showed that ranked trabecular number and trabecular separation in the OVX-Soy+FOS+Dried Plum group were marginally or significantly higher than in the OVX-Casein, OVX-Casein+FOS+Green Tea and OVX-casein+FOS+Dried Plum+Green Tea groups but were not different from the OVX-Casein+FOS+Dried Plum, OVX-Casein+FOS and OVX-Casein+Dried Plum groups. Again no differences were seen for ranked trabecular thickness. Additionally, an ANOVA using Dunnett's test showed that ranked trabecular number and trabecular separation in the SHAM-Casein group were significantly higher than all the ovariectomized rat treatment groups except the OVX-Soy+FOS+Dried Plum group but was not higher for ranked trabecular thickness. For ranked trabecular number and trabecular separation, GLM contrast t-tests demonstrated that they were significantly higher for dried plum alone versus no dried plum, were marginally higher for FOS alone versus no FOS, were significantly higher for the FOS+dried plum combination versus neither FOS nor dried plum but were not different from FOS alone or dried plum alone suggesting that, for each measure, there exist individual ingredients effects but not an added combination effect. Bolstering the evidence for a FOS+dried plum combination effect for ranked trabecular number and trabecular separation is that the OVX-Casein+FOS+Dried group is marginally higher than OVX-Casein for both measures. There were no differences found for ranked trabecular thickness for any FOS, dried plum or FOS+dried plum combination effects, however. Also for ranked trabecular number and trabecular separation, GLM contrast t-tests demonstrated that there were no differences between the soy and casein protein sources or between dried plum and green tea polyphenol sources. However, there was a combination effect of dried plum+green tea in lowering ranked trabecular thickness as evidenced by dried plum+green tea combination being marginally lower than neither dried plum nor green tea, marginally lower than dried plum alone and significantly lower than green tea alone.

Connective Density and Structural Model Index (SMI)

GLM contrast t-tests showed that, with the SHAM-Casein group, ranked connective density was significantly higher and ranked SMI significantly lower than ranked connective density and ranked SMI in the OVX-Casein group. ANOVAs using Dunnett's test showed that ranked connective density in the OVX-Soy+FOS+Dried Plum group was significantly higher than the OVX-Casein, OVX-Casein+FOS+Green Tea and OVX-Casein+FOS+Dried Plum+Green Tea groups but was not different from the OVX-Casein+FOS+Dried Plum, OVX-Casein+FOS and OVX-casein+Dried Plum groups; no differences were seen for ranked SMI. Additionally, ANO-VAs using Dunnett's test showed that ranked connective density in the SHAM-Casein group was significantly higher than all the ovariectomized rat treatment groups except the OVX-Soy+FOS+Dried Plum group and ranked SMI in the SHAM-Casein group was significantly lower than all the ovariectomized groups except the OVX-Casein+FOS+Dried Plum group. For ranked connective density, GLM contrast t-tests demonstrated that they were marginally higher for both dried plum alone versus no dried plum and for FOS alone versus no FOS, were significantly higher for the FOS+dried plum combination versus neither FOS nor dried plum but were not different from FOS alone or dried plum alone suggesting that, for each measure, there exist individual ingredients effects but not an added combination effect. Bolstering the evidence for a FOS+dried plum combination effect for ranked connective density is that the OVX-Casein+FOS+Dried Plum group is marginally higher than OVX-Casein. The results for ranked SMI are similar except that there is more of a dried plum and less of an FOS effect in that there is no difference between FOS alone and no FOS, and a significantly lowering effect of dried plum alone versus no dried plum. For ranked connective density and ranked SMI, GLM contrast t-tests also demonstrated that there were no differences between the soy and casein protein sources but, with ranked connective density, dried plum alone was a marginally better polyphenol source than green tea alone. GLM contrast t-tests demonstrated that dried plum was significantly better as a polyphenol source in lowering ranked SMI compared to green tea with the findings that dried plum alone was significantly lower than green tea alone and also significantly lower than the dried plum+green tea combination.

Discussion

The primary objective of Experiment II was to confirm that feeding a dietary combination of soy, FOS, and dried plum could reverse osteopenia. Osteopenia was induced by ovariectomy and confirmed via DEXA measurements of the whole body 46 days post ovariectomy. Serum levels for estradiol also confirmed that ovariectomy was successful. The effects of the dietary treatments on cancerous and cortical bone were assessed by bone mineral density, bone mineral content and indices of bone morphometry. Reversing established osteopenia is far more difficult to accomplish via dietary means than to prevent bone loss.

Results from both Experiment I and II appear to be the first to show a reversal of established osteopenia due to estrogen deficiency with a combination of soy, FOS and low dose dried plum. Using Tukey's, this was demonstrated by increases in whole body and spine BMD and whole body BMC to levels not statistically significantly different from SHAM.

A synergistic effect to reverse osteopenia of the spine was observed with treatments containing FOS and dried plum. Spine BMD was greater for the combination than feeding FOS alone (p=0.017) or dried plum alone (p=0.072). Synergy was also noted in the change in bone mineral density from the OVX control (baseline) to treatments with FOS+Dried plum as compared to FOS alone and to dried plum alone, in bone density values from whole body, femur, and spine.

The FOS and dried plum combination also had positive effects on the supporting bone variables. Lumbar spine % ash was higher for the combination compared to no dried plum or FOS or dried plum alone. Femur bone magnesium was greater in animals treated with FOS/dried plum. Deoxypyridinoline, a marker of bone resorption, was nominally lowered in treatment groups compared to OVX-casein control. It was significantly lowered by green tea catechins but this treatment did not restore BMD, BMC or microstructural properties.

IGF-1 is associated with bone formation and lean body mass anabolism. Levels were increased by OVX but were significantly lowered by FOS alone. However, it was not affected by dried plum alone or FOS/dried plum combination. This suggests that the combination is able to maintain the high rate of bone formation. The elevated IGF-1 levels may also have been responsible for the higher body weights and lean body mass observed among OVX groups. The results showed that gain in lean body mass during the treatment period was marginally higher with FOS/dried plum compared to no FOS or dried plum suggesting that dried plum more than FOS contributes to increasing lean body mass. Lean body mass at the end of the study was not different for groups treated with FOS or FOS/green tea or FOS/green tea/dried plum.

Stability of bone depends on the structure of the trabecular network rather than on bone mineral content. Therefore, the trabecular network of the proximal tibia was also analyzed by X-ray micro computed tomography and bone histomorphometry. This dietary combination of soy/FOS/dried plum also improved bone quality, i.e., bone volume/total volume, trabecular number and connective density were not significantly different from SHAM. From a structural point of view, a number of studies have indicated that treatment should be initiated before a considerable loss of trabecular bone has occurred. Therefore, it is possible that the soy+FOS+plum treatment would also have a greater beneficial effect on structural properties of other bones rich in trabeculae such as lumbar vertebrae.

One objective of this study was to determine if the protein source had an effect on reversing osteopenia. Historically, soy protein containing products have taste challenges. Conceivably, the organoleptic challenges would be less if the protein sources in a bone health product could be a blend of soy and casein. Analysis by GLM t-tests showed that increases in whole body, spine and femur BMD and BMC, as well as for the different indices of bone histomorphometry, was not dependent on the protein source. However, when soy was present with FOS and dried plum instead of casein, values were nominally and consistently higher.

Another objective of this study was to investigate the effect of other sources of polyphenolic compounds on osteopenia. We chose green tea catechins because they are 150 times more potent in antioxidant capacity than dried plum powder. Our hypothesis was that green tea catechins, by decreasing cyclooxygenase activity, would decrease bone resorption and would result in improved bone density compared to OVX-Casein controls and OVX-dried plum. Cyclo oxygenase activity regulates PGE2 which acts as a stimulator of osteoclast function and osteclastogenesis. PGE2 is necessary for normal bone remodeling but high levels of PGE2 increase bone resorption. Proinflammatory cytokines (TNF-alpha, IL-1, IL-6) are among the most potent stimulators of bone resorption known and are elevated in estrogen deficiency and postmenopause. They directly through the stimulation of other local factors intervene with every single step in osteoclatogenesis that determines the rate of bone resorption, from the proliferation and differentiation of the early osteoclast precursor cell to the resorption capacity and the lifespan of the mature osteoclast. Although animals treated with green tea catechins had significantly lower levels of deoxypyridinoline (a marker of bone resorption), results on whole body and spine BMD showed that dried plum was superior to green tea catechins since dried plum alone was significantly higher than green tea/FOS alone and higher than dried plum+green tea combo. Effects on femur BMD, femur bone calcium and magnesium, and for several indices of histomorphometry also showed the dried plum was superior to green tea. TNF-alpha and IL-1 were measured in this study but there were no significant effects by diet on either cytokine. This may have been due to a lack of sensitivity of the assays since no differences were detected due to ovariectomy or because of the large variability in the data. Another explanation may be due to a greater suppression of COX-2 by green tea catechins below levels that are needed for normal bone remodeling. Although bone density levels were not significantly different from SHAM with FOS/dried plum, adding green tea to the combination significantly reduced bone density to levels similar to OVX-controls.

Conclusions

1. A synergistic increase in bone mineral density (whole body, femur, and spine) from an OVX baseline was noted for the combination of dried fruit solids (e.g. dried plum solids) and a soluble, indigestible oligosaccharide (e.g., FOS), as compared to either ingredient alone, all in a casein-based diet (see Table—Experiment II—Summary of Results).
2. The combination of soy protein with dried plum and FOS favorably modulates bone metabolism, resulting in increased bone mineral density, bone mineral content and improved microstructural properties in an osteopenic rat model.
3. There was no significant difference between soy+FOS+plum and casein+FOS+plum on increasing spine, femur or whole body BMD. However, soy+FOS+plum had the most pronounced effect on bone quality since this combination was able to increase whole body BMD, whole body BMC and several parameters of micro-CT to levels not statistically different from SHAM animals.
4. The results showed that dried plum was superior to green tea in its ability to raise BMD. Although tea catechins suppressed urinary excretion of Dpd, a specific marker of bone resorption, they did not influence bone density or microstructural properties of the examined bones.

Experiment III

The purpose of this experiment was to identify which component of dried plum contained bone bioactivity, i.e., skin, flesh, juice or polyphenols, to identify other potential sources (e.g., raisin, fig, date, blueberries, beta-hydroxy beta methylbutyrate or HMB) that exhibit bone bioactivity and to understand if osteopenia can be reversed with a lower dose of FOS and dried plum than was used previously.

After five days of acclimatization, study animals were randomly assigned to one of 15 groups (n=10/group) and placed in individual cages. Rats were either sham-operated (SHAM) or ovariectomized (OVX) and fed casein-based diets for forty days. To ensure that sufficient bone loss has occurred in the OVX animals, bone mineral density was assessed via Dual Energy X-ray Absorptiometry (DEXA) prior to treatment. Groups 1 and 2 were fed casein-based diets throughout the entire length of the study and served as the control groups. Treatments were initiated for Groups 3-15 forty days post ovariectomy surgery and followed for 60 days. Bone mineral density was assessed before and after treatments. Two days prior to the termination of the study, rats were placed in individual metabolic cages and urine was collected from 18:00 h-6:00 h. During this period, the rats had no access to food. Urine was collected in acid-washed tubes, acidified with 0.03 ml of 6 mol/L of HCl per ml of urine and the total volume was measured. At the end of the study, the rats were anesthetized with ketomine and xylazine (intraperitoneally; 100 mg and 5 mg/kg body weight, respectively) and exsanguinated. Blood was collected, serum separated and aliquoted in small samples. All urine and plasma samples were frozen at −20° C. until analyses. Femurs and 3-5 lumbar spine were dissected out for bone analyses. Initial and weekly body weights were measured. Sham animals were fed ad libitum and their precise food intakes were measured every three days. Before each feeding, the food remaining was weighed and the amount ingested was calculated. Rats in the other groups were pair-fed to the mean intake of the sham animals and had free access to deionized water.

The design was a randomized, prospective, single-blind, positive controlled, parallel study. Control groups were fed a casein-based diet. Treatment groups were fed semi-purified diets containing casein, fructooligosaccharides, whole dried plum powder or dried plum polyphenol solids, dried plum juice solids, dried plum puree solids, dried plum skin solids or raisin solids or fig solids or date solids or blueberry solids or HMB. The treatment groups are outlined in following table:

Example III: Treatment Groups

| Group | Surgery | FOS | Test Ingredient |
|---|---|---|---|
| 1 | SHAM | 0 | 0 |
| 2 | OVX | 0 | 0 (control) |
| 3 | OVX | 2% | 0 |
| 4 | OVX | 5% | 7.5% Whole Dried Plum powder |
| 5 | OVX | 2% | 5.0% Whole Dried Plum powder |
| 6 | OVX | 2% | Dried Plum Polyphenols equivalent to 7.5% Dried Plum powder |
| 7 | OVX | 2% | 7.5% Dried Plum Juice |
| 8 | OVX | 2% | 7.5% Dried plum puree |
| 9 | OVX | 2% | 7.5% Dried plum pulp/skins |
| 10 | OVX | 2% | 7.5% Raisin powder |
| 11 | OVX | 2% | 7.5% Fig powder |
| 12 | OVX | 2% | 7.5% Date powder |
| 13 | OVX | 2% | 7.5% Blueberry powder |
| 14 | OVX | 2% | 0.25% HMB |
| 15 | OVX | 0 | 0.25% HMB |

One hundred fifty, (n=10/group) ninety day old Harlan Sprague-Dawley, 210 gm, female rats were purchased from Harlan Sprague Dawley Inc. (Indianapolis, Ind.). Upon arrival at the institution, rats were individually housed in stainless steel wire mesh cages in an environmentally controlled animal laboratory at 25° C. with a 12 h light-dark cycle. The rats had free access to deionized water and semi-purified diets. They were handled according to National Institutes of Health guidelines for humane treatment of experimental animals. They were observed for five days prior to the study for signs of illness by the animal technician responsible for providing husbandry.

The composition of the semi-purified casein-based diets are described in the following table. To ensure equivalency, the diets were assayed for carbohydrate, protein, fat, calcium and phosphorus content prior to the feeding protocol. All diets were prepared to be isonitrogenous, isocaloric and equivalent in calcium and phosphorus content. The diets consisted of approximately 22% protein, 67% carbohydrate and 11% fat. The treatment diets also contained 7.5% or 5% (w/w) dried plum powder (Sunsweet Growers, Inc., Pleasanton, Calif.), or 7.5% (w/w) dried plum solids from juice concentrate (Sunsweet Growers, Inc., Pleasanton, Calif.), or 7.5% (w/w) dried plum solids from puree (Sunsweet Growers, Inc., Pleasanton, Calif.), or 7.5% (w/w) dried plum solids from pulp/skins (Sunsweet Growers, Inc., Pleasanton, Calif.), or dried plum polyphenols equivalent to 7.5% (w/w) dried plum powder, or 7.5% (w/w) raisin solids (Mid America), or 7.5% (w/w) fig solids (Mid America), or 7.5% (w/w) date solids (Mid America), or 7.5% (w/w) blueberry solids (Mid America), or 0.25% (w/w) HMB (Metabolic Technologies, Inc., Ames, Iowa) and 5% or 2% (w/w) short chain fructooligosaccharides (NutraFlora®, FOS Golden Technologies, Inc). Diets were stored at 5° C. Food consumption data was collected from days 6-4o. Sham animals were fed ad libitum and their precise food intakes were measured every three days. Before each feeding, the food remaining was weighed and the amount ingested was calculated. Rats in the other groups were pair-fed to the mean intake of the sham animals and had free access to deionized water. The compositions of the diets for the various groups are shown in the following tables:

| Ingredient | Group 1 | Group 2 | Group 3 | Group 4 | Group 5 | Group 6 | Group 7 | Group 8 |
|---|---|---|---|---|---|---|---|---|
| | | | | gm/kg diet | | | | |
| Casein† | 227 | 227 | 227 | 226.5 | 226.7 | 227 | 224.5 | 224 |
| Dried Plum Powder | — | — | — | 75 | 50 | — | — | — |
| Dried Plum‡ Polyphenols | — | — | — | — | — | 247 | — | — |
| Dried Plum Juice Solids | — | — | — | — | — | — | 115 | — |
| Dried Plum puree Solids | — | — | — | — | — | — | — | 115 |
| Dried Plum Pulp Solids | — | — | — | — | — | — | — | — |
| Raisin Solids | — | — | — | — | — | — | — | — |
| Fig Solids | — | — | — | — | — | — | — | — |
| Date Solids | — | — | — | — | — | — | — | — |
| Blueberry Solids | — | — | — | — | — | — | — | — |
| HMB | — | — | — | — | — | — | — | — |
| FOS | — | — | 20 | 50 | 20 | 20 | 20 | 20 |
| Sucrose | 417 | 417 | 417 | 417 | 417 | 178 | 417 | 417 |
| Cornstarch | 200 | 200 | 180 | 95 | 143.3 | 180 | 128.3 | 126 |
| Cellulose | 56 | 56 | 56 | 48.6 | 51 | 56 | 51 | 52.2 |
| Canola oil | 57 | 57 | 57 | 53.5 | 54.7 | 56.8 | 56.8 | 56.6 |
| Vitamin§ Mixture | 10 | 10 | 10 | 10 | 10 | 10 | 10 | 10 |
| Mineral¶ Mixture | 13.4 | 13.4 | 13.4 | 13.4 | 13.4 | 13.4 | 13.4 | 13.4 |
| Calcium** Carbonate | 10 | 10 | 10 | 9.4 | 9.6 | 9.8 | 9.9 | 9.9 |
| Sodium** phosphate dibasic | 3.9 | 3.9 | 3.9 | 3.6 | 3.7 | 3.4 | 3.7 | 3.7 |
| Potassium** phosphate monobasic | 2.4 | 2.4 | 2.4 | 2.2 | 2.2 | 2.0 | 2.2 | 2.2 |
| Potassium citrate monohydrate | 0.9 | 0.9 | 0.9 | 0.9 | 0.9 | 0.9 | 0.9 | 0.9 |
| Choline bitartrate | 2.5 | 2.5 | 2.5 | 2.5 | 2.5 | 2.5 | 2.5 | 2.5 |
| L-cysteine | 1.8 | 1.8 | 1.8 | 1.8 | 1.8 | 1.8 | 1.8 | 1.8 |

| Ingredient | Group 9 | Group 10 | Group 11 | Group 12 | Group 13 | Group 14 | Group 15 |
|---|---|---|---|---|---|---|---|
| | | | | gm/kg diet | | | |
| Casein† | 226.1 | 224.1 | 223.3 | 225.1 | 226.2 | 227 | 227 |
| Dried Plum Powder | — | — | — | — | — | — | — |
| Dried Plum‡ Polyphenols | — | — | — | — | — | — | — |
| Dried Plum Juice Solids | — | — | — | — | — | — | — |
| Dried Plum Paste Solids | — | — | — | — | — | — | — |
| Dried Plum Pulp Solids | 75 | — | — | — | — | — | — |
| Raisin Solids | — | 75 | — | — | — | — | — |
| Fig Solids | — | — | 75 | — | — | — | — |
| Date Solids | — | — | — | 75 | — | — | — |
| Blueberry Solids | — | — | — | — | 75 | — | — |
| HMB | — | — | — | — | — | 2.57 | 2.57 |
| FOS | 20 | 20 | 20 | 20 | 20 | 20 | 0 |
| Sucrose | 417 | 417 | 417 | 417 | 417 | 417 | 417 |
| Cornstarch | 130.8 | 119.5 | 126.8 | 119.2 | 120.5 | 178 | 198 |
| Cellulose | 41 | 52.3 | 46.8 | 50.4 | 49.3 | 56 | 56 |
| Canola oil | 53.8 | 55.9 | 55.3 | 56 | 55 | 57 | 57 |
| Vitamin§ Mixture | 10 | 10 | 10 | 10 | 10 | 10 | 10 |
| Mineral¶ Mixture | 13.4 | 13.4 | 13.4 | 13.4 | 13.4 | 13.4 | 13.4 |
| Calcium** Carbonate | 9.6 | 9.7 | 9.3 | 9.8 | 9.8 | 9.2 | 9.2 |
| Sodium** phosphate dibasic | 3.6 | 3.7 | 3.7 | 3.8 | 3.7 | 3.9 | 3.9 |
| Potassium** phosphate monobasic | 2.2 | 2.2 | 2.2 | 2.2 | 2.2 | 2.40 | 2.40 |
| Potassium citrate monohydrate | 0.9 | 0.9 | 0.9 | 0.9 | 0.9 | 0.9 | 0.9 |

| -continued | | | | | | | |
|---|---|---|---|---|---|---|---|
| Choline bitartrate | 2.5 | 2.5 | 2.5 | 2.5 | 2.5 | 2.5 | 2.5 |
| L-cysteine | 1.8 | 1.8 | 1.8 | 1.8 | 1.8 | 1.8 | 1.8 |

*Diets provide 0.4% calcium, 0.3% phosphorus.
†Casein provides 0.72% phosphorus.
‡Dried Plum extract plus maltodextrin as carrier provides 5.18 mg gallic acid equivalents/g.
§Vitamin mixture obtained from Harlan Tekland.
¶Mineral mixture is Calcium and phosphorous deficient
**Calcium carbonate contains 40.04% calcium; potassium phosphate monobasic contains 22.76% phosphorus; sodium phosphate dibasic contains 21.82% phosphorus.

Effectiveness of treatment was determined by the changes in bone mineral density, bone calcium and phosphorus content, and micro-computed tomography between control groups (SHAM and OVX casein) and treatment groups. A summary of the results is shown in the following tables:

| | Group 1 SHAM Casein diet | Group 2 OVX Casein diet | Group 3 2% FOS | Group 4 5% FOS/7.5% DP PWD |
|---|---|---|---|---|
| | Bone mineral density (Mean ± SE) | | | |
| Whole body | 0.16823 ± 0.00175a | 0.16175 ± 0.00102ab | 0.16486 ± 0.00235ab | 0.16540 ± 0.00143ab |
| Femur | 0.24147 ± 0.00385a | 0.22387 ± 0.00250b | 0.22570 ± 0.00337ab | 0.22938 ± 0.00213ab |
| Spine | 0.26650 ± 0.00359a | 0.23236 ± 0.00308c | 0.24395 ± 0.00395bc | 0.24927 ± 0.00312b |
| | Change in Bone mineral density (from Baseline) | | | |
| Whole body | 0.00265 ± 0.00098b | 0.00390 ± 0.00109ab | 0.00572 ± 0.00154ab | 0.01024 ± 0.00114a |
| | Bone mineral content (LS Mean ± SE) | | | |
| Whole body | 9.7087 ± 0.17925 | 10.0798 ± 0.16359 | 10.1752 ± 0.23533 | 10.1868 ± 0.14511 |
| Femur | 0.44999 ± 0.01133 | 0.42578 ± 0.00841 | 0.44581 ± 0.01590 | 0.43810 ± 0.01104 |
| Spine | 0.13561 ± 0.00436 | 0.12108 ± 0.00355 | 0.12872 ± 0.00580 | 0.12775 ± 0.00426 |
| | Bone Volume/Total Volume (Ranked) Mean ± SE | | | |
| | 0.28475 ± 0.02208a | 0.12170 ± 0.00703b | 0.12052 ± 0.00939b | 0.14534 ± 0.00555b |
| | Trabecular No. (1/mm) (Ranked) Mean ± SE | | | |
| | 5.05712 ± 0.14966a | 1.66868 ± 0.07283c | 1.84265 ± 0.12671bc | 2.22128 ± 0.07063bc |
| | Trabecular separation (mm) (Ranked) Mean ± SE | | | |
| | 0.18967 ± 0.00670e | 0.64214 ± 0.02568a | 0.59387 ± 0.04054abc | 0.47589 ± 0.02035cd |
| | Connective Density (Ranked) Mean ± SE | | | |
| | 132.771 ± 6.756a | 32.868 ± 1.860b | 34.169 ± 2.957b | 44.604 ± 2.143b |
| | Structural Model Index (Ranked) Mean ± SE | | | |
| | 1.04158 ± 0.19856b | 1.87187 ± 0.06408a | 1.90853 ± 0.08900a | 1.84483 ± 0.05654a |
| Body Weight Gain during Treatment period Mean ± SE | 37.7 ± 11.4 | 31.7 ± 3.3 | 26.5 ± 3.3 | 27.5 ± 3.1 |

| | Group 5 2% FOS/5% DP PWD | Group 6 2% FOS/DP Polyphenol | Group 7 2% FOS/DP Juice | Group 8 2% FOS/DP Puree |
|---|---|---|---|---|
| | Bone mineral density (Mean ± SE) | | | |
| Whole body | 0.16238 ± 0.00216ab | 0.16407 ± 0.00130ab | 0.16207 ± 0.00137ab | 0.16164 ± 0.00134ab |
| Femur | 0.22752 ± 0.00331ab | 0.22576 ± 0.00242ab | 0.22941 ± 0.00354ab | 0.22362 ± 0.00264b |
| Spine | 0.24182 ± 0.00339bc | 0.24201 ± 0.00373bc | 0.24435 ± 0.00357bc | 0.24222 ± 0.00334bc |

-continued

| | | Change in Bone mineral density (from Baseline) | | |
|---|---|---|---|---|
| Whole body | 0.00583 ± 0.00180ab | 0.00564 ± 0.00146ab | 0.00538 ± 0.00164ab | 0.00752 ± 0.00211ab |
| | | Bone mineral content (LS Mean ± SE) | | |
| Whole body | 10.0789 ± 0.18478 | 10.0898 ± 0.16321 | 9.7606 ± 0.19030 | 9.8663 ± 0.11220 |
| Femur | 0.42898 ± 0.01098 | 0.42585 ± 0.00719 | 0.41260 ± 0.01437 | 0.41470 ± 0.01043 |
| Spine | 0.12836 ± 0.00519 | 0.12599 ± 0.00454 | 0.12670 ± 0.00491 | 0.11700 ± 0.00363 |
| | | Bone Volume/Total Volume (Ranked) Mean ± SE | | |
| | 0.13491 ± 0.01130b | 0.13860 ± 0.00659b | 0.15405 ± 0.02818b | 0.12486 ± 0.00707b |
| | | Trabecular No. (1/mm) (Ranked) Mean ± SE | | |
| | 1.94445 ± 0.16500bc | 2.16385 ± 0.10330bc | 2.37533 ± 0.36138b | 1.92019 ± 0.07148bc |
| | | Trabecular separation (mm) (Ranked) Mean ± SE | | |
| | 0.56071 ± 0.03605abc | 0.48773 ± 0.02412bcd | 0.49788 ± 0.05122bcd | 0.55195 ± 0.02403abc |
| | | Connective Density (Ranked) Mean ± SE | | |
| | 38.475 ± 3.062b | 39.303 ± 2.107b | 47.061 ± 1357b | 36.480 ± 2.020b |
| | | Structural Model Index (Ranked) Mean ± SE | | |
| | 1.8305 ± 0.05508a | 1.91423 ± 0.07301a | 1.77531 ± 0.19574a | 1.92806 ± 0.05451a |
| Body Weight Gain during Treatment period Mean ± SE | 33.3 ± 3.5 | 28.1 ± 3.7 | 22.4 ± 3.6 | 25.8 ± 2.9 |

| | Group 9 2% FOS/DP Pulp/Skins | Group 10 2% FOS/7.5% Raisin | Group 11 2% FOS/7.5% Fig | Group 12 2% FOS/7.5% Date |
|---|---|---|---|---|
| | | Bone mineral density (Mean ± SE) | | |
| Whole body | 0.16015 ± 0.00180b | 0.15975 ± 0.00174b | 0.16004 ± 0.00104b | 0.16211 ± 0.00149ab |
| Femur | 0.22393 ± 0.00473b | 0.22442 ± 0.00415b | 0.21864 ± 0.00307B | 0.22941 ± 0.00308ab |
| Spine | 0.23951 ± 0.00265bc | 0.23727 ± 0.00271bc | 0.23567 ± 0.00373bc | 0.23986 ± 0.00278bc |
| | | Change in Bone mineral density (from Baseline) | | |
| Whole body | 0.00328 ± 0.00199ab | 0.00377 ± 0.00174ab | 0.00507 ± 0.00191ab | 0.00504 ± 0.00148ab |
| | | Bone mineral content (LS Mean ± SE) | | |
| Whole body | 9.9016 ± 0.15217 | 9.9653 ± 0.18153 | 9.6808 ± 0.10319 | 10.2122 ± 0.16112 |
| Femur | 0.42122 ± 0.01567 | 0.41561 ± 0.01454 | 0.40420 ± 0.01186 | 0.43559 ± 0.01086 |
| Spine | 0.12326 ± 0.00434 | 0.12512 ± 0.00327 | 0.11541 ± 0.00325 | 0.12428 ± 0.00337 |
| | | Bone Volume/Total Volume (Ranked) Mean ± SE | | |
| | 0.11740 ± 0.00760b | 0.12472 ± 0.00725b | 0.10510 ± 0.00571b | 0.12720 ± 0.00615b |
| | | Trabecular No. (1/mm) (Ranked) Mean ± SE | | |
| | 1.90702 ± 0.09054bc | 1.83242 ± 0.07325bc | 1.70261 ± 0.06247c | 1.79491 ± 0.06409bc |
| | | Trabecular separation (mm) (Ranked) Mean ± SE | | |
| | 0.56559 ± 0.03213abc | 0.57736 ± 0.02263abc | 0.62035 ± 0.02284ab | 0.59351 ± 0.02221abc |
| | | Connective Density (Ranked) Mean ± SE | | |
| | 29.919 ± 2.248b | 35.832 ± 2.384b | 29.143 ± 1.617b | 35.871 ± 1.427b |
| | | Structural Model Index (Ranked) Mean ± SE | | |
| | 2.02252 ± 0.0627a | 1.92846 ± 0.04625a | 2.08644 ± 0.05065a | 1.88462 ± 0.05563a |
| Body Weight Gain during Treatment period Mean ± SE | 29.8 ± 2.8 | 23.7 ± 4.4 | 23.5 ± 3.7 | 33.5 ± 4.0 |

-continued

| | Group 13 2% FOS/7.5% Blueberry | Group 14 2% FOS/HMB | Group 15 HMB |
|---|---|---|---|
| | Bone mineral density (Mean ± SE) | | |
| Whole body | 0.16016 ± 0.00111b | 0.16074 ± 0.00164ab | 0.15989 ± 0.00160b |
| Femur | 0.22502 ± 0.00314b | 0.22536 ± 0.00262ab | 0.21983 ± 0.00293b |
| Spine | 0.23704 ± 0.00371bc | 0.23447 ± 0.00357bc | 0.23408 ± 0.00350bc |
| | Change in Bone mineral density (from Baseline) | | |
| Whole body | 0.00485 ± 0.00085ab | 0.00469 ± 0.00091ab | 0.00298 ± 0.00144ab |
| | Bone mineral content (LS Mean ± SE) | | |
| Whole body | 9.7476 ± 0.16833 | 9.7795 ± 0.18122 | 9.7590 ± 0.13232 |
| Femur | 0.42399 ± 0.01166 | 0.42012 ± 0.01345 | 0.41553 ± 0.00996 |
| Spine | 0.11671 ± 0.00281 | 0.11764 ± 0.00348 | 0.11875 ± 0.00419 |
| | Bone Volume/Total Volume (Ranked) Mean ± SE | | |
| | 0.11695 ± 0.00605b | 0.11942 ± 0.00476b | 0.11407 ± 0.00658b |
| | Trabecular No. (1/mm) (Ranked) Mean ± SE | | |
| | 1.80867 ± 0.07434bc | 1.80457 ± 0.08490bc | 1.64891 ± 0.07800c |
| | Trabecular separation (mm) (Ranked) Mean ± SE | | |
| | 0.58363 ± 0.02399abc | 0.57922 ± 0.02612abc | 0.65546 ± 0.03361a |
| | Connective Density (Ranked) Mean ± SE | | |
| | 31.171 ± 2.029b | 31.817 ± 1.603b | 32.865 ± 2.472b |
| | Structural Model Index (Ranked) Mean ± SE | | |
| | 2.02226 ± 0.03905a | 1.89267 ± 0.02967a | 1.93138 ± 0.04093a |
| Body Weight Gain during Treatment period Mean ± SE | 27.8 ± 3.4 | 32.8 ± 3.4 | 29.0 ± 6.9 |

Experiment III

Results

A) Whole Body Bone Mineral Density—Final

From the Tukey analysis, SHAM-Casein is significantly greater than OVX+FOS+Dried Plum Pulp/Skins, OVX+FOS+Raisin, OVX+FOS+Fig, OVX+FOS+Blueberry, and OVX+HMB.

From the Dunnett's analysis, SHAM-Casein is significantly greater than OVX-Casein, OVX+FOS+Dried Plum Puree, OVX+FOS+Dried Plum Pulp/Skins, OVX+FOS+Raisin, OVX+FOS+Fig, OVX+FOS+Blueberry, OVX+FOS+HMB, and OVX+HMB.

From the contrast statements from the appropriate analysis, the following findings were made:

SHAM-Casein is significantly greater than OVX-Casein.

OVX+FOS is significantly greater than OVX+FOS+Dried Plum Pulp/Skins, OVX+FOS+Raisin, OVX+FOS+Fig, OVX+FOS+Blueberry, and OVX+HMB.

OVX+5% FOS+7.5% Dried Plum Powder is significantly greater than OVX+FOS+Dried Plum Pulp/Skins, OVX+FOS+Raisin, OVX+FOS+Fig, OVX+FOS+Blueberry, OVX+FOS+HMB, and OVX+HMB.

B) Whole Body Bone Mineral Density—Change from Baseline to Final

From the Tukey analysis, OVX+5% FOS+7.5% Dried Plum Powder is significantly greater than SHAM-Casein.

From the Dunnett's analysis, OVX+5% FOS+7.5% Dried Plum Powder is significantly greater than SHAM-Casein.

From the contrast statements from the appropriate analysis, the following findings were made:

OVX+5% FOS+7.5% Dried Plum Powder is significantly greater than OVX-Casein, OVX+FOS, OVX+2% FOS+5% Dried Plum Powder, OVX+FOS+Dried Plum Juice, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.

C) Whole Body Bone Mineral Density—Percent Change from Baseline to Final

From the Tukey analysis, OVX+5% FOS+7.5% Dried Plum Powder is significantly greater than SHAM-Casein.

From the Dunnett's analysis, OVX+5% FOS+7.5% Dried Plum Powder is significantly greater than SHAM-Casein.

From the contrast statements from the appropriate analysis, the following findings were made:

OVX+5% FOS+7.5% Dried Plum Powder is significantly greater than OVX-Casein, OVX+FOS, OVX+2% FOS+5% Dried Plum Powder, OVX+FOS+Dried Plum Polyphenols, OVX+FOS+Dried Plum Juice, OVX+

FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.

(i) Fourth Lumbar Bone Mineral Density

From the Tukey analysis, SHAM-Casein is significantly greater than OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB. In addition, OVX+5% FOS+7.5% Dried Plum Powder is significantly greater than OVX-Casein.

From the Dunnett's analysis, SHAM-Casein is significantly greater than OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.

From the contrast statements from the appropriate analysis, the following findings were made:
- SHAM-Casein is significantly greater than OVX-Casein.
- OVX+FOS is significantly greater than OVX-Casein and OVX+HMB.
- OVX+5% FOS+7.5% Dried Plum Powder is significantly greater than OVX-Casein, OVX+FOS+Dried Plum Pulp/Skins, OVX+FOS+Raisin, OVX+FOS+Fig, OVX+FOS+Blueberry, OVX+FOS+HMB, and OVX+HMB.
- OVX+FOS+Dried Plum Polyphenols is significantly greater than OVX-Casein.
- OVX+FOS+Dried Plum Juice is significantly greater than OVX-Casein.
- OVX+FOS+Dried Plum Puree is significantly greater than OVX-Casein.

(ii) Whole Body Bone Mineral Content—Final

From the model including all treatment groups, there is a significant treatment group effect (p=0.0063). Because a covariate was used in the analysis, Tukey and Dunnett's test were not performed. From the contrast statements from the appropriate analysis, the following findings were made:
- SHAM-Casein is significantly greater than OVX-Casein.
- OVX+FOS is significantly greater than OVX+FOS+Dried Plum Pulp/Skins, OVX+FOS+Raisin, OVX+FOS+Fig, and OVX+HMB.
- OVX+5% FOS+7.5% Dried Plum Powder is significantly greater than OVX+FOS+Dried Plum Pulp/Skins, OVX+FOS+Raisin, OVX+FOS+Fig, OVX+FOS+Blueberry, and OVX+HMB.

(iii) Fourth Lumbar Bone Mineral Content

From the model including all treatment groups, there is a significant treatment group effect (p<0.0001). Because a covariate was used in the analysis, Tukey and Dunnett's test were not performed. From the contrast statements from the appropriate analysis, the following findings were made:
- SHAM-Casein is significantly greater than OVX-Casein.
- OVX+FOS is significantly greater than OVX-Casein.
- OVX+5% FOS+7.5% Dried Plum Powder is significantly greater than OVX-Casein, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.
- OVX+FOS+Dried Plum Polyphenols is significantly greater than OVX-Casein.
- OVX+FOS+Dried Plum Juice is significantly greater than OVX-Casein.
- OVX+FOS+Dried Plum Puree is significantly greater than OVX-Casein.

(iv) Right Femur Bone Mineral Density

From the Tukey analysis, SHAM-Casein is significantly greater than OVX-Casein, OVX+FOS+Dried Plum Puree, OVX+FOS+Dried Plum Pulp/Skins, OVX+FOS+Raisin, OVX+FOS+Fig, OVX+FOS+Blueberry, and OVX+HMB.

From the Dunnett's analysis, SHAM-Casein is significantly greater than OVX-Casein, OVX+FOS, OVX+2% FOS+5% Dried Plum Powder, OVX+FOS+Dried Plum Polyphenols, OVX+FOS+Dried Plum Puree, OVX+FOS+Dried Plum Pulp/Skins, OVX+FOS+Raisin, OVX+FOS+Fig, OVX+FOS+Blueberry, OVX+FOS+HMB, and OVX+HMB.

From the contrast statements from the appropriate analysis, the following findings were made:
- SHAM-Casein is significantly greater than OVX-Casein.
- OVX+5% FOS+7.5% Dried Plum Powder is significantly greater than OVX+FOS+Fig and OVX+HMB.
- OVX+2% FOS+5% Dried Plum Powder is significantly greater than OVX+FOS+Fig.
- OVX+FOS+Date is significantly greater than OVX+FOS+Fig.

(v) Weight—Change from Study Day 1 to Pre-Switch to Regular Treatment

From the Tukey analysis, OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB are significantly greater than SHAM-Casein.

From the Dunnett's analysis, OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB are significantly greater than SHAM-Casein.

From the contrast statements from the appropriate analysis, the following findings were made:
- OVX-Casein is significantly greater than SHAM-Casein.
- OVX+FOS is significantly greater than OVX+FOS+Dried Plum Juice, OVX+FOS+Fig, OVX+FOS+Blueberry, and OVX+FOS+HMB.
- OVX+FOS+Raisin is significantly greater than OVX+FOS+HMB.
- OVX+FOS+Date is significantly greater than OVX+FOS+HMB.

(vi) Weight—Change from Pre-Switch to Regular Treatment to End of Study

From the Wilcoxon two-sample rank-sum test, the following findings were made:
- OVX+2% FOS+5% Dried Plum Powder is significantly greater than OVX+FOS+Dried Plum Juice and OVX+FOS+Raisin.

(vii) Average Intake from Study Day 1 to Baseline

From the Wilcoxon two-sample rank-sum test, there are no significant differences among treatment groups.

(viii) Average Intake from Baseline to Final

From the Wilcoxon two-sample rank-sum test, the following findings were made:

OVX-Casein is significantly greater than OVX+FOS+Blueberry and OVX+HMB.

(ix) Bone Volume/Total Volume

From the Tukey analysis, SHAM-Casein is significantly greater than OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.

From the Dunnett's analysis, SHAM-Casein is significantly greater than OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.

From the contrast statements from the appropriate analysis, the following findings were made:

SHAM-Casein is significantly greater than OVX-Casein.

OVX+5% FOS+7.5% Dried Plum Powder is significantly greater than OVX+FOS, OVX+FOS+Raisin, OVX+FOS+Fig, OVX+FOS+Blueberry, OVX+FOS+HMB, and OVX+HMB.

OVX+2% FOS+5% Dried Plum Powder is significantly greater than OVX+FOS+Fig and OVX+HMB.

OVX+FOS+Dried Plum Juice is significantly greater than OVX+FOS+Dried Plum Pulp/Skins.

OVX+FOS+Date is significantly greater than OVX+FOS+Fig.

(x) Connective Density

From the Tukey analysis, SHAM-Casein is significantly greater than OVX-Casein, OVX+FOS, OVX+5% FOS+7-5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.

From the Dunnett's analysis, SHAM-Casein is significantly greater than OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.

From the contrast statements from the appropriate analysis, the following findings were made:

SHAMS-Casein is significantly greater than OVX-Casein.

OVX+5% FOS+7.5% Dried Plum Powder is significantly greater than OVX-Casein, OVX+FOS, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.

OVX+2% FOS+5% Dried Plum Powder is significantly greater than OVX+FOS+Fig, OVX+FOS+Blueberry, and OVX+FOS+HMB.

OVX+FOS+Dried Plum Juice is significantly greater than OVX-Casein and OVX+FOS+Dried Plum Pulp/Skins.

OVX+FOS+Raisin is significantly greater than OVX+FOS+Fig.

OVX+FOS+Date is significantly greater than OVX+FOS+Fig.

(xi) Structure Model Index

From the Tukey analysis, OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB are significantly greater than SHAM-Casein.

From the Dunnett's analysis, OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB are significantly greater than SHAM-Casein.

From the contrast statements from the appropriate analysis, the following findings were made:

OVX-Casein is significantly greater than SHAM-Casein.

OVX+FOS+Fig is significantly greater than OVX-Casein, OVX+FOS, OVX+5% FOS+7.5% Dried Plum Powder, OVX+2% FOS+5% Dried Plum Powder, OVX+FOS+Raisin, OVX+FOS+Date, and OVX+FOS+HMB.

OVX+FOS+Blueberry is significantly greater than OVX+5% FOS+7.5% Dried Plum Powder and OVX+2% FOS+5% Dried Plum Powder.

(xi) Trabecular Number

From the Tukey analysis, SHAM-Casein is significantly greater than OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB. In addition, OVX+FOS+Dried Plum Juice is significantly greater than OVX-casein, OVX+FOS+Fig, and OVX+HMB.

From the Dunnett's analysis, SHAM-Casein is significantly greater than OVX-casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB.

From the contrast statements from the appropriate analysis, the following findings were made:

SHAM-Casein is significantly greater than OVX-Casein.

OVX+5% FOS+7.5% Dried Plum Powder is significantly greater than OVX-Casein, OVX+FOS, OVX+FOS+Raisin, OVX+FOS+Fig, OVX+FOS+Date, OVX+FOS+Blueberry, OVX+FOS+HMB, and OVX+HMB.

OVX+2% FOS+5% Dried Plum Powder is significantly greater than OVX+HMB.

OVX+FOS+Dried Plum Polyphenols is significantly greater than OVX-Casein.

OVX+FOS+Dried Plum Juice is significantly greater than OVX-Casein, OVX+FOS, OVX+FOS+Dried Plum Puree, and OVX+FOS+Dried Plum Pulp/Skins.

(xii) Trabecular Thickness

From the Tukey analysis, there are no significant differences among treatment groups. From the Dunnett's analysis, there are no significant differences among treatment groups. From the contrast statements from the appropriate analysis, there are no significant differences among treatment groups.

(xiii) Trabecular Separation

From the Tukey analysis, OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB are significantly greater than SHAM-Casein. In addition, OVX-Casein and OVX+HMB are significantly greater than OVX+5% FOS+7.5% Dried Plum Powder, OVX+FOS+Dried Plum Polyphenols, and OVX+FOS+Dried Plum Juice. Also, OVX+FOS+Fig is significantly greater than OVX+5% FOS+7.5% Dried Plum Powder.

From the Dunnett's analysis, OVX-Casein, OVX+FOS, OVX+5% FOS+7.5% Dried Plum Powder, OVX+2% FOS+5% Dried Plum Powder, OVX+FOS+Dried Plum Polyphenols, OVX+FOS+Dried Plum Juice, OVX+FOS+Dried Plum Puree, OVX+FOS+Dried Plum Pulp/Skins, OVX+FOS+Raisin, OVX+FOS+Fig, OVX+FOS+Date, OVX+FOS+Blueberry, OVX+FOS+HMB, and OVX+HMB are significantly greater than SHAM-Casein.

From the contrast statements from the appropriate analysis, the following findings were made:

- OVX-Casein is significantly greater than SHAM-Casein, OVX+5% FOS+7.5% Dried Plum Powder, OVX+FOS+Dried Plum Polyphenols, and OVX+FOS+Dried Plum Juice.
- OVX+FOS is significantly greater than OVX+5% FOS+7.5% Dried Plum Powder, OVX+FOS+Dried Plum Polyphenols and OVX+FOS+Dried Plum Juice.
- OVX+FOS+Raisin, OVX+FOS+Fig, OVX+FOS+Date, OVX+FOS+Blueberry, OVX+FOS+HMB, and OVX+HMB are significantly greater than OVX+5% FOS+7.5% Dried Plum Powder.
- OVX+HMB is significantly greater than OVX+2% FOS+5% Dried Plum Powder.

Discussion

The previous experiments have shown that not only does the combination of 5% FOS+7.5% dried plum powder reverse osteopenia but that the effect is synergistic, i.e., the increase in BMD is greater than the sum effect of the single ingredients. As an extension to these learnings, we wanted to understand if the bone bioactivity of dried plum was confined to a component in the whole fruit or if the efficacy is dependent on the whole fruit. The practical application for finding activity in other dried plum components would result in more viable product forms with varying sensory attributes as well as a cost reduction from having to use 100% dried plum powder in a product. Hence, we selected to test 7.5% (wt/wt) solids from prune juice concentrate, puree (flesh), polyphenol extract, and skins/pulp, a byproduct of juice production. These were all tested in combination with 2% FOS (wt/wt). Two percent FOS (wt/wt) in the animal diet represents approximately a human consumption of 8 grams/day which has been shown to illicit a physiological change in the gut microflora and an acute increase in calcium absorption.

Different dried plum products varied in their bone bioactivity, producing results in all or some of the bones tested, i.e., lumbar spine/trabecular bone, femur bone or whole body. Since lumbar spine is rich in trabecular bone, effects of treatment would appear at this site before they would appear in cortical bone such as in the femur. This was the case with the dried plum products. Pair wise comparisons for spine BMD showed that 5% FOS+7.5% DP powder, 2% FOS+5% DP powder, 2% FOS+DP polyphenols, 2% FOS+DP juice and 2% FOS+DP puree were statistically greater than OVX-control, but not for 2% FOS+skins/pulp. Dunnett's analysis showed that final whole body BMD was similar to SHAM for all dried plum products except puree and pulp/skins. However, linear contrasts showed a non-significant difference for percent change from baseline in whole body BMD in animals treated with 2% FOS+7.5% DP puree (5.02%) and 5% FOS+7.5% dried plum powder (6.62%). Femur bones, which are rich in cortical bone and the most difficult to affect were responsive to only two of the dried plum treatments, 5% FOS+7.5% dried plum powder and 2% FOS+DP juice were not significantly different from SHAM.

The effects on bone mineral density by dried plum and FOS combinations are also supported by micro-computed tomography data. Because of the sensitivity of micro computed tomography, changes in bone microarchitecture can be identified long before changes in bone mineral density are measurable. The groups consuming the highest dose of dried plum powder and DP juice+FOS had values statistically different from OVX-control for connective density, trabecular number and trabecular separation. Effects on percent bone volume approached statistical significance. Groups consuming polyphenols, puree or low dose DP powder also had values for trabecular number and trabecular separation that were statistically different or approaching significance as compared to OVX-control. Pairwise comparison to 2% FOS alone showed that high dose DP Powder+2% FOS was statistically higher for percent bone volume, connective density, trabecular number, and trabecular separation, DP juice+FOS was statistically higher for trabecular number and separation, and DP polyphenols was statistically higher for trabecular separation. These data support the effect of whole dried plum as well as its components to preserve the microarchitecture of bones and also supports previous work that showed the combination of FOS and DP powder is critical for retention of bone mass.

There may be several different mechanisms by which the whole dried plum maintains or improves bone integrity better than its individual parts. Out of all the dried plum products tested, 2% FOS+DP Pulp/Skins had the least effect on reversing osteopenia and was not statistically different from OVX-control. Since this is a byproduct of juice production, it contains negligible amounts of polyphenols, sugar alcohols and saccharides, components that are present in the other dried plum products and may be important for mineral absorption. Furthermore, micro CT data showed that the individual components of dried plum powder, i.e., juice, puree and polyphenols, preserve the microarchitecture of trabecular bone while pulp/skins did not.

To address the secondary objective of the study of identifying other potential sources that could reverse osteopenia, treatment groups containing combinations of 2% FOS with fruit solids from raisin, fig, date, blueberries, HMB or HMB alone were tested against OVX control; 2% FOS, 2% FOS+5% DP Powder and 5% FOS+7.5% DP Powder treatment groups. There were no statistically significant differences in change from baseline whole body BMD, lumbar spine or femur bone mineral density compared to OVX-control or 2%

FOS. Pair-wise comparisons showed the group treated with 5% FOS+7.5% DP Powder had significantly higher spine BMD than all of the groups containing the other potential sources, however, there were no significant differences between these sources and the group treated with 2% FOS+ 5% DP Powder. Femur BMD was not statistically significantly different for raisin, date, blueberry, and HMB/FOS compared to 5% FOS+7.5% DP Powder probably because cortical bone (femur) is most resistant to physiological changes. Animals treated with date powder had whole body BMC and femur BMD not significantly different from 5% FOS+7-5% DP Powder or SHAM and connective density not different from 2% FOS+5% DP Powder. Serum and lumbar magnesium was significantly higher for blueberry and date than OVX. The lack of significant effects on reversal of osteopenia by raisin, fig, date and blueberry in this study may have been due to the dose and/or short treatment period.

Raisin powder showed effects on several outcome measures that are conducive to bone anabolism, i.e., serum magnesium, urine calcium, and lumbar calcium were significantly higher, compared to OVX-control. Serum IGF-1 levels were almost significantly higher (p=0.0548). High urinary calcium is indicative of higher calcium absorption and consequently resulted in higher lumbar spine calcium. High levels of IGF-1 has an anabolic effect on bone mass. This group also experienced less weight gain than OVX-control (p=0.0753). The prevention of ovariectomy-induced weight gain may be due to raisin's high isoflavone content (1836 micrograms/kg). When isoflavones are fed with scFOS, their bioavailability is increased and consequently so will the phytoestrogenic activity.

The effect of HMB on bone has not been previously studied. It was hypothesized that HMB could support bone mass since studies have shown that HMB increases lean body mass and protein is a large component of bone. We observed similar body composition effects that have been reported earlier, i.e., the HMB group had significantly less fat gain during the treatment period compared to OVX-control but the addition of FOS ameliorated this effect. There were significant increases in IGF-1 compared to OVX-control, which is indicative of anabolism; however, there were no significant effects on BMD. In this study, animals treated with HMB had the lowest change, other than SHAM, from baseline in whole body BMD and the lowest urinary calcium excretion. The addition of FOS did not improve whole body, spine or femur BMD but significantly lowered urinary deoxypyridinoline (DPD) excretion compared to HMB alone. Furthermore, treatment with HMB/FOS resulted in significantly lower femur calcium compared to OVX-control and HMB alone but % bone volume, connective density, SMI, trabecular number, trabecular thickness, and trabecular separation did not differ between HMB and HMB/FOS groups.

To address the third objective of the study for understanding if osteopenia can be reversed with a lower dose of FOS and DP powder, animals treated with 2% FOS+5% DP powder were compared to animals treated with 5% FOS+7.5% DP powder and OVX-control. The results reported in this study showed that the effect on a bony site varied with the dose of DP powder and FOS. The highest dose of dried plum powder in combination with the highest dose of FOS (5% FOS+7.5% DP powder) had a consistent effect to reverse osteopenia in the whole body, femur and spine. The high dose produced a 6.6% increase from baseline in whole body BMD which was significantly greater compared to OVX-control, 2% FOS and 2% FOS+5% DP powder. Spine BMD was significantly greater than OVX for both high and low doses (p=0.0572) of FOS and DP powder and there were no significant differences between the doses. Femur BMD was not different from Sham for high dose FOS/DP powder and linear contrasts showed that there were no significant differences on femur BMD between high and low doses.

Although animals were pair-fed to the SHAM group, weight change during the treatment period was not equivalent among groups. Groups treated with 2% FOS+DP juice and 2% FOS+raisin had less weight gain than either the OVX or SHAM groups, p=0.06 and p=0.07, respectively. Animals treated with fig had one of the lowest weight changes as well. There was 25%, 26%, and 29% less weight gain, compared to OVX, by fig, raisin and dried plum, respectively. Most of the weight gain was due to lean mass and not fat mass since all treatments, with the exception of date, produced less fat gain. Animals treated with 2% FOS+DP juice had statistically significant less fat gain during the treatment period. Therefore, the benefits of the nutrient combinations that have been investigated in this study include protection from bone loss as well as inhibition of weight gain due to estrogen deficiency.

Conclusions from the Study:

1. The results of this study met the first objective which was to identify the bone bioactivity of the individual components of dried plum. Reversal of spine osteopenia was accomplished by 5% FOS+7.5% DP powder, 2% FOS+DP polyphenols, 2% FOS+DP juice and 2% FOS+DP puree, but not for 2% FOS+skins/pulp, as compared to OVX. The highest gains in whole body BMD were by animals treated with 5% FOS+7.5% DP powder and 2% FOS+DP puree. Retention of the trabecular microarchitecture was observed by all dried plum products except for skins/pulp. Consequently, bone bioactivity exists in all components of dried plum tested except for the skins/pulp, the byproduct of juice production.

2. The second objective was to identify other potential sources for bone bioactivity. Although the combination of 2% FOS and 7.5% solids from raisin, fig, date, and blueberries did not increase whole body or spine BMD above OVX-controls or 2% FOS, there was an increase in lumbar spine calcium content by raisin, increases in serum and lumbar spine magnesium by blueberry and date and lumbar spine phosphorus by fig. HMB did not reverse established osteopenia and had the highest levels of bone resorption.

3. The third objective was to identify reversal of osteopenia by a lower dose of FOS and DP powder. The highest dose (5% FOS+7.5% DP powder) had consistent and significant effects to reverse osteopenia in the whole body, femur and spine and most microarchitecture parameters. Reversal of osteopenia by low dose dried plum (DP) powder and FOS varied on the bony site. Compared to OVX, low dose had no significant effect on whole body and femur BMD and an almost significant effect on spine (p=0.0572). There was no significant difference between doses to retain connective density in trabecular bone. Consequently, a low dose would have to be fed for longer periods of time to show effects on other microarchitecture parameters in this animal model of post-menopause osteoporosis.

4. Results from this study also support the use of the combination of dried plum solids and FOS over using 2% FOS alone for the reversal of osteopenia and retention of microarchitectural structure.

5. Decrease in weight gain during the treatment period by DP juice, raisin and fig were an unexpected finding. The benefit of combining dried fruit solids with FOS is not only bone protective but may help decrease weight gain due to estrogen deficiency in this animal model of post-menopause osteoporosis.

EXAMPLES

The following examples illustrate specific embodiments of the nutritional compositions and methods of the present invention, including some suitable techniques to prepare the compositions. The examples are given solely for the purpose of illustration and are not to be construed as limitations of the present invention, as many variations thereof are possible without departing from the spirit and scope of the invention.

Each of the exemplified compositions is administered to women or other individuals for treatment or prevention of osteoporosis, and or to manage weight in estrogen-insufficient individuals. The individuals consume at least one serving of the exemplified product every day to provide each of them with 1-35 g/day of soluble, indigestible oligosaccharide, from 1-50 g/day of dried fruit solids, and for some embodiments an additional 1-160 g/day of soy protein and/or an additional 1-50 g/day of flaxseed. The individuals consume the product every day, in single or divided doses, for at least 6 months, with additional instruction to continue taking the product as recommended beyond the 6 month period for long term bone health benefits in the treatment or prevention of osteoporosis. For estrogen-insufficient individuals interested in weight control, either weight loss or maintenance, the product may be consumed for a specified period of time to achieve the desired body weight, or consumed indefinitely or as otherwise needed for weight maintenance, while maintaining or reducing total calorie intake.

Example 1

Nutritional Bar

Exemplified are nutritional bar embodiments of the present invention, and a method of using the compositions in individuals to treat or prevent osteoporosis, or to control weight in estrogen-insufficient individuals, in accordance with the methods of the present invention.

The bars are prepared from the ingredients described below. In order to prepare the bar, the dry ingredients (Supro 661, FOS, dried plum, soy crisp 60%/o, apples, DCP and ground flaxseed) are weighed and added into a large mixing bowl. The dry ingredients are blended for 1 minute until well mixed. In a separate bowl, fructose and sorbitol are added to the liquid ingredients (HFCS 55, corn syrup 42 DE, sorbitol 70%, plum puree and rice syrup). The liquid ingredients are mixed together for 1-2 minutes. Apple flavor, cinnamon hazelnut (IFF) and vanillin are added to the liquid ingredients and mixed for approximately one minute. The mixed liquid ingredients are then added to the blended dry ingredients and mixed until completely blended. The dough that forms is removed from the mixing bowl and kneaded to ensure that it is completely mixed. The dough is then placed onto a rolling mat and rolled to approximately ½ inch in thickness. The dough is cut into rectangular pieces each weighing approximately 47 grams and baked. A coating is melted utilizing a kettle or double boiler, and is then added to a pastry bag and then drizzled on top of the bar using about 2.5-3.5 grams of coating per bar. The bars are allowed to cool and are then covered with wrapping.

From 1 to 6 of the bars, most typically 1-2 bars, are consumed by each individual on a daily basis to treat or prevent osteoporosis in accordance with the methods of the present invention. These exemplified bars are supplemental nutrition sources, but are also formulated with a balance of vitamins, minerals, and macronutrients as a potentially sole source of nutrition as well.

From 1-2 bars are consumed daily by estrogen-insufficient individuals, without an increase in total calories consumed each day, with a resulting weight loss over a period of 3-6 months, or continuous use for weight maintenance while maintaining or reducing total calorie intake.

Ingredient Listing: Nutritional Bars

| Ingredient | Ex. 1.1 | Ex. 1.2 | Ex. 1.3 | Ex. 1.4 | Ex. 1.5 |
|---|---|---|---|---|---|
| | | | Wt/wt % | | |
| Coating (Kerny) | 10.12 | 10.12 | 10.12 | 10.12 | 10.12 |
| High Fructose Corn Syrup 55 (Cargill) | 3.20 | 3.20 | 3.20 | 3.20 | 3.20 |
| Corn Syrup 42 DE (Cargill) | 1.78 | 1.78 | 1.78 | 1.78 | 1.78 |
| Soy Protein Isolate (Solae) | 12.11 | 12.11 | 12.11 | 12.11 | 12.11 |
| Soy Crisp (80% protein)(Solae) | 8.09 | 8.09 | 8.09 | 8.09 | 8.09 |
| Sorbitol 70% (SPI) | 1.05 | 1.05 | 1.05 | 1.05 | 1.05 |
| FOS (Golden Technologies) | 8.00 | 8.00 | 8.00 | 8.00 | — |
| XOS | — | — | — | — | 8.00 |
| Dried Plum (Sunsweet) | 21.18 | — | — | — | 21.18 |
| Dried grape (*Vitus vinifera*, Thompson variety) | — | 30.18 | — | — | — |
| Dried figs (*Picus carcica*, Kudata variety) | — | — | 30.18 | — | — |
| Dried dates (*Phoenix dactylifera*, *Arecaceae* variety) | — | — | — | 30.18 | — |
| Plum Puree | 9.00 | — | — | — | 9.00 |
| Apples, evaporated diced (FDP) | 4.62 | 4.62 | 4.62 | 4.62 | 4.62 |
| DCP | 1.77 | 1.77 | 1.77 | 1.77 | 1.77 |
| Fructose | 1.15 | 1.15 | 1.15 | 1.15 | 1.15 |
| Rice Syrup | 10.80 | 10.80 | 10.80 | 10.80 | 10.80 |
| Vitamin/mineral premix | 0.52 | 0.52 | 0.52 | 0.52 | 0.52 |
| Ground Flaxseed (Hesko) | 6.01 | 6.01 | 6.01 | 6.01 | 6.01 |
| Cinnamon Hazelnut Flavor (IFF) | 0.43 | 0.43 | 0.43 | 0.43 | 0.43 |
| Apple Flavor (Firmenich) | 0.05 | 0.05 | 0.05 | 0.05 | 0.05 |
| Vanillin | 0.10 | 0.10 | 0.10 | 0.10 | 0.10 |

Example 2

Low pH Smoothie

Exemplified is a nutritional embodiment of the present invention in the form of a low-pH smoothie. The composition is prepared by conventional methods for preparing a nutritional composition in a smoothie product form. All ingredient amounts are listed as kg per 1000 kg batch, unless otherwise specified.

| Ingredient Listing: Low pH Smoothie | |
|---|---|
| Ingredient | Amount |
| Fruit and Flax Combination | 94.464200 |
| 1. Dried Plum Powder/Plum Puree/Plum Paste | |
| 2. Ground Flaxseed | |
| Sucrose | 18.600000 |
| Soy protein isolate | 19.6500000 |
| Sodium caseinate (Miprodan) | 10.220000 |
| Lodex 15 (maltodextrin) | 10.116600 |
| Pectin (JMJ type) | 9.000000 |
| Citric acid | 4.786500 |
| Potassium citrate | 3.983300 |
| High oleic safflower oil | 3.040000 |
| Inulin or GOS | 17.00 |
| Micronized tricalcium phosphate | 4.800000 |
| Phosphoric acid (as 75% soln) | 2.734700 |
| Sodium citrate | 2.466600 |
| Avicel ® (microcrystalline cellulose) | 2.000000 |
| Magnesium chloride | 1.750000 |
| Ascorbic acid | 0.441661 |
| Magnesium phosphate | 1.600000 |
| UTM/TM premix (ultra trace mineral/trace mineral) | 0.363757 |
| Canola oil | 0.350000 |
| Lecithin | 0.112400 |
| Acesulfame K | 0.110200 |
| Lycopene (as 20% suspension) | 0.097000 |
| Vitamin D, E, K premix | 0.065433 |
| Water soluble vitamin premix | 0.072685 |
| Vitamin A palmitate | 0.008245 |
| Water | QS |
| Total | 1000.000000 |

Example 3

Milk-Based Beverage

The following example illustrates milk-based nutritional liquid embodiments of the present invention. The ingredients for each exemplified composition are described in the following tables. All ingredient amounts are listed as kg per 1000 kg batch of product, unless otherwise specified. The milk-based beverages are prepared by forming at least three separate slurries (e.g., carbohydrate-mineral slurry, protein-in-water slurry, protein-in-fat slurry) which are then blended together, heat-treated, and standardized. The resulting composition is then flavored, aseptically packaged into plastic bottles or retort sterilized.

| Ingredient Listing: Milk-based Beverage | | | | | | |
|---|---|---|---|---|---|---|
| Ingredient | Example 3.1 | Example 3.2 | Example 3.3 | Example 3.4 | Example 3.5 | Example 3.6 |
| Water | Q.S. | Q.S. | Q.S. | Q.S. | Q.S. | Q.S. |
| Sucrose | 38.9 | 32.9 | 34.9 | 38.9 | 32.9 | 34.9 |
| FOS | — | — | — | 14 | 14 | 10 |
| Dried plum powder | 8 | 8 | 16 | 8 | 8 | 16 |
| Dried raisin powder | 14 | 14 | 34.9 | — | — | — |
| Flaxseed (ground, Golden) | — | 14 | — | — | 14 | — |
| High oleic safflower oil | 39.8 | 39.8 | 39.8 | 39.8 | 39.8 | |
| Milk protein isolate | 33.4 | 33.4 | 33.4 | 33.4 | 33.4 | 33.4 |
| Acid casein | 9.44 | 9.44 | 9.44 | 9.44 | 9.44 | 9.44 |
| Magnesium phosphate dibasic | 6.74 | 6.74 | 6.74 | 6.74 | 6.74 | 6.74 |
| Whey protein concentrate | 5.28 | 5.28 | 5.28 | 5.28 | 5.28 | 5.28 |
| Micronized-tri calcium phosphate | 4.27 | 4.27 | 4.27 | 4.27 | 4.27 | 4.27 |
| Avicel | 4.00 | 4.00 | 4.00 | 4.00 | 4.00 | 4.00 |
| Lemon cream | 4.00 | 4.00 | 4.00 | 4.00 | 4.00 | 4.00 |
| Sodium chloride | 2.11 | 2.11 | 2.11 | 2.11 | 2.11 | 2.11 |
| Soy lecithin | 1.66 | 1.66 | 1.66 | 1.66 | 1.66 | 1.66 |
| Potassium citrate | 1.63 | 1.63 | 1.63 | 1.63 | 1.63 | 1.63 |
| Sodium citrate | 1.05 | 1.05 | 1.05 | 1.05 | 1.05 | 1.05 |
| Lemon oil | 0.500 | 0.500 | 0.500 | 0.500 | 0.500 | 0.500 |
| Carrageenan - Viscarin SD-389 | 0.400 | 0.400 | 0.400 | 0.400 | 0.400 | 0.400 |
| Sensient Tumeric Concentrate #3285 | 0.200 | 0.200 | 0.200 | 0.200 | 0.200 | 0.200 |
| Sodium Hydroxide | 0.196 | 0.196 | 0.196 | 0.196 | 0.196 | 0.196 |
| Liquid Sucralose | 0.175 | 0.175 | 0.175 | 0.175 | 0.175 | 0.175 |
| Ascorbyl palmitate | 0.0498 | 0.0498 | 0.0498 | 0.0498 | 0.0498 | 0.0498 |
| Acesulfame potassium | 0.0350 | 0.0350 | 0.0350 | 0.0350 | 0.0350 | 0.0350 |

-continued

| | | | Ingredient Listing: Milk-based Beverage | | | |
|---|---|---|---|---|---|---|
| Ingredient | Example 3.1 | Example 3.2 | Example 3.3 | Example 3.4 | Example 3.5 | Example 3.6 |
| Pyridoxine hydrochloride ($B_6$) | 0.0299 | 0.0299 | 0.0299 | 0.0299 | 0.0299 | 0.0299 |
| Tocopherol-2 antioxidant | 0.00830 | 0.00830 | 0.00830 | 0.00830 | 0.00830 | 0.00830 |
| Folic Acid | 0.00500 | 0.00500 | 0.00500 | 0.00500 | 0.00500 | 0.00500 |
| Vitamin $D_3$ | 0.00300 | 0.00300 | 0.00300 | 0.00300 | 0.00300 | 0.00300 |
| Cyanocobalamin | 0.000337 | 0.000337 | 0.000337 | 0.000337 | 0.000337 | 0.000337 |

Example 4

Soy-Based Beverage

The following example illustrates soy-based nutritional liquid embodiments of the present invention. The ingredients for each exemplified composition are described in the following tables. All ingredient amounts are listed as kg per 1000 kg batch of product, unless otherwise specified.

Ingredient Listing: Soy-based Beverage

| Ingredient | Example 2.1 | Example 2.2 | Example 2.3 | Example 2.4 | Example 2.5 |
|---|---|---|---|---|---|
| Water | Q.S. | Q.S. | Q.S. | Q.S. | Q.S. |
| Maltodextrin M-100 | 48.300000 | 42.252000 | 32.252000 | 22.252000 | 0 |
| Maltitol syrup | 33.070000 | 33.070000 | 33.070000 | 33.070000 | 33.070000 |
| Acid casein | 29.429910 | 29.429910 | 29.429910 | 29.429910 | 29.429910 |
| Fructose | 26.900000 | 26.900000 | 26.900000 | 26.900000 | 26.900000 |
| High oleic safflower oil | 29.085000 | 29.085000 | 29.085000 | 29.085000 | 29.085000 |
| Soy protein isolate | 8.7195200 | 8.7195200 | 8.7195200 | 8.7195200 | 8.7195200 |
| Dried plum powder | 10 | 20 | 30 | 10 | 20 |
| Flaxseed, ground | — | — | 10 | 10 | 20 |
| FOS | 15 | 30 | 40 | 15 | 30 |
| Calcium caseinate | 5.5966600 | 5.5966600 | 5.5966600 | 5.5966600 | 5.5966600 |
| m-Tricalcium phosphate | 2.8000000 | 2.8000000 | 2.8000000 | 2.8000000 | 2.8000000 |
| Magnesium chloride | 2.2000000 | 2.2000000 | 2.2000000 | 2.2000000 | 2.2000000 |
| Flavor | 1.8000441 | 1.8000441 | 1.8000441 | 1.8000441 | 1.8000441 |
| Canola oil | 3.4218000 | 3.4218000 | 3.4218000 | 3.4218000 | 3.4218000 |
| Soy lecithin | 1.7109000 | 1.7109000 | 1.7109000 | 1.7109000 | 1.7109000 |
| Sodium citrate | 1.3580000 | 1.3580000 | 1.3580000 | 1.3580000 | 1.3580000 |
| Magnesium phosphate dibasic | 1.0280000 | 1.0280000 | 1.0280000 | 1.0280000 | 1.0280000 |
| Ascorbic acid | 0.7884000 | 0.7884000 | 0.7884000 | 0.7884000 | 0.7884000 |
| Potassium chloride | 0.8000000 | 0.8000000 | 0.8000000 | 0.8000000 | 0.8000000 |
| Potassium phosphate dibasic | 0.7000000 | 0.7000000 | 0.7000000 | 0.7000000 | 0.7000000 |
| Choline Chloride | 0.4720020 | 0.4720020 | 0.4720020 | 0.4720020 | 0.4720020 |
| UTM/TM Premix | 0.4407000 | 0.4407000 | 0.4407000 | 0.4407000 | 0.4407000 |
| Vitamin E | 0.0990080 | 0.0990080 | 0.0990080 | 0.0990080 | 0.0990080 |
| Water soluble vitamin premix | 0.0974210 | 0.0974210 | 0.0974210 | 0.0974210 | 0.0974210 |
| Gellan gum | 0.0750000 | 0.0750000 | 0.0750000 | 0.0750000 | 0.0750000 |
| Acesulfame K | 0.0749560 | 0.0749560 | 0.0749560 | 0.0749560 | 0.0749560 |
| Lutein, 5% in Corn Oil | 0.0692325 | 0.0692325 | 0.0692325 | 0.0692325 | 0.0692325 |

-continued

| Ingredient | Example 2.1 | Example 2.2 | Example 2.3 | Example 2.4 | Example 2.5 |
|---|---|---|---|---|---|
| Vitamins DEK premix | 0.0650353 | 0.0650353 | 0.0650353 | 0.0650353 | 0.0650353 |
| Beta-Carotene | 0.0089100 | 0.0089100 | 0.0089100 | 0.0089100 | 0.0089100 |
| Vitamin A | 0.0063475 | 0.0063475 | 0.0063475 | 0.0063475 | 0.0063475 |

The soy-based beverage is prepared by combining the carbohydrate/mineral ingredients with heat at 155° F. A separate protein solution is prepared with the protein solution ingredients with heat at 140° F., and a separate fat solution is prepared with heat at 120° F. The three formed solutions are then combined in a blend tank, and subjected to the following process steps:

deaerate the mix at 10-15 inches of Hg
using a positive pump, pump blend mix through a plate heater
heat mix to 160-180° F.
UHT treatment preheat mix to 208-220° F.
Heat mix to 295°±2° F. (steam injection), hold time 5 seconds
Flash cool mix to 208-220° F.
Cool mix further to 160-170° F.
Homogenize mix at 3900-4100/400-600 psig
Hold mix at 165-185° F. for 16 seconds
Cool the mix to 34-44° F.

The cooled mixture is standardized and then packaged and subjected to retort processing in 8 oz metal cans.

Example 5

Other Product Forms

Many other nutritional compositions of the present invention, such as those exemplified below, are formulated as oral dietary or similar other product forms, and then administered to individuals to treat or prevent osteoporosis in such individuals, and/or to lose or maintain weight in estrogen-insufficient individuals. These other nutritional compositions all contain FOS or other soluble, indigestible oligosaccharide as described herein, in combination with dried plum solids or other dried fruit solids as also defined herein. Such other nutritional products are used by individuals on a daily basis, most often 1-2 times daily as a snack or with meals, to provide or help provide each individual with 1-35 g/day of FOS or other soluble, indigestible oligosaccharide and from 1-50 g/day of dried plum solids or other dried fruit solids. Each of the exemplified product forms can be easily prepared by one of ordinary skill in the nutrition or formulation arts by conventional methods or techniques specific to each desired product form.

| Product | Dried Plum Powder (wt/wt %) | | FOS (wt/wt %) | | Flaxseed (wt/wt %) | | Soy protein (wt/wt %) | |
|---|---|---|---|---|---|---|---|---|
| Breakfast cereal | 0.5-50 | 1-10 | 1-20 | 1-10 | 0-50 | 0.5-25 | 0-50 | 1-25 |
| Sauces, jams, jelly, coffee creamer | 0.5-80 | 1-40 | 5-40 | 5-20 | 0-80 | 0.5-40 | 0-80 | 1-40 |
| Pasta | 0.5-30 | 1-15 | 1-20 | 1-10 | 0-30 | 0.5-15 | 0-30 | 1-15 |
| Whole grain or other flower | 0.5-50 | 1-25 | 1-20 | 1-10 | 0-50 | 0.5-25 | 0-50 | 1-25 |
| Salted snacks | 0.5-50 | 1-25 | 1-20 | 1-10 | 0-50 | 0.5-25 | 0-50 | 1-25 |
| Ice-cream | 0.5-60 | 1-30 | 1-30 | 1-15 | 0-60 | 0.5-30 | 0-60 | 1-30 |
| Bread, bagels, pastries, cakes | 0.5-50 | 1-25 | 1-20 | 1-10 | 0-50 | 0.5-25 | 0-50 | 1-25 |
| Dry mixes-cakes, pancakes, muffins | 0.5-50 | 1-25 | 1-20 | 1-10 | 0-50 | 0.5-25 | 0-50 | 1-25 |
| Processed meat | 0.5-40 | 1-20 | 1-20 | 1-10 | 0-40 | 0.5-40 | 0-40 | 1-20 |
| Pizza | 0.5-50 | 1-25 | 1-20 | 1-10 | 0-50 | 0.5-25 | 0-50 | 1-25 |
| Yogurt | 0.5-50 | 1-25 | 1-30 | 1-15 | 0-50 | 0.5-25 | 0-50 | 1-25 |

What is claimed is:

1. A method for controlling body weight in women with estrogen insufficiency, said method comprising administering at least one serving per day to a woman with estrogen insufficiency a nutritional composition comprising:
    (A) dried plum solids comprising flavonoids, hydroxycinnamic acid, and a fiber component of which at least about 20% by weight is soluble fiber, and
    (B) a soluble, indigestible oligosaccharide in addition to the fiber component from the dried plum solids; wherein the administration provides from about 20 to about 100 grams per day of dried plum solids and from about 3 to about 30 grams per day of the soluble, indigestible oligosaccharide.

2. The method of claim 1, wherein total daily caloric intake for the estrogen-insufficient woman is maintained or reduced.

3. The method of claim 2, wherein the estrogen insufficiency is caused by menopause, ovarictomy, ovarian disorders and drug treatments.

4. The method of claim 1, wherein the dried plum solids and the soluble, indigestible oligosaccharide together represent from about 50% to 100% by weight of total carbohydrate in the nutritional composition, and the weight ratio of the dried plum solids to the soluble, indigestible oligosaccharide is from about 15:1 to about 1:15.

5. The method of claim 1, wherein the dried plum solids have a soluble fiber content of from about 30% to about 70% by weight of total dietary fiber in the dried plum solids.

6. The method of claim 1, wherein the soluble, indigestible oligosaccharide comprises fructooligosaccharides.

7. The method of claim 1, wherein the nutritional composition is a solid bar comprising from about 20% to about 40% by weight of the dried plum solids and from about 3% to about 30% by weight of the soluble, indigestible oligosaccharide.

8. The method of claim 1, wherein the nutritional composition comprises fat, protein, carbohydrates, vitamins, and minerals.

9. A method for controlling weight gain in estrogen-insufficient women, said method comprising administering at least one serving per day to a woman with estrogen insufficiency a nutritional composition comprising:
  (A) dried plum solids, and
  (B) a soluble, indigestible oligosaccharide component separate from and in addition to the dried plum solids; wherein the administration provides from about 20 to about 100 grams per day of dried plum solids and from about 3 to about 30 grams per day of the soluble, indigestible oligosaccharide.

10. The method of claim 9, wherein the dried plum solids and the soluble, indigestible oligosaccharide together represent from about 50% to 100% by weight of total carbohydrate in the nutritional composition, and the weight ratio of the dried plum solids to the soluble, indigestible oligosaccharide is from about 15:1 to about 1:15.

11. The method of claim 9, wherein the dried plum solids have a soluble fiber content of from about 30% to about 70% by weight of total dietary fiber in the dried plum solids.

12. The method of claim 9, wherein the indigestible oligosaccharide comprises fructooligosaccharides.

13. The method of claim 9, wherein the nutritional composition is a solid nutritional bar comprising from about 20% to about 40% by weight of the dried plum solids and from about 3% to about 30% by weight of the soluble, indigestible oligosaccharide.

14. The method of claim 9, wherein the total daily caloric intake for the estrogen-insufficient woman is maintained or reduced.

* * * * *